(12) United States Patent
Krishnaswamy et al.

(10) Patent No.: US 10,555,791 B2
(45) Date of Patent: Feb. 11, 2020

(54) DEVICES FOR GUIDING TISSUE TREATMENT AND/OR TISSUE REMOVAL PROCEDURES

(71) Applicant: CairnSurgical, Inc., Lebanon, NH (US)

(72) Inventors: Venkataramanan Krishnaswamy, Lebanon, NH (US); Robert F. Rioux, Ashland, MA (US); David Danielsen, Westborough, MA (US); George Bourne, Boston, MA (US)

(73) Assignee: CairnSurgical, Inc., Lebanon, NH (US)

( * ) Notice: Subject to any disclaimer, the term of this patent is extended or adjusted under 35 U.S.C. 154(b) by 0 days.

(21) Appl. No.: 16/437,915

(22) Filed: Jun. 11, 2019

(65) Prior Publication Data
US 2019/0350668 A1 Nov. 21, 2019

Related U.S. Application Data

(63) Continuation of application No. PCT/US2016/029708, filed on Apr. 29, 2019.
(Continued)

(51) Int. Cl.
*A61B 90/17* (2016.01)
*A61B 34/20* (2016.01)
(Continued)

(52) U.S. Cl.
CPC .......... *A61B 90/17* (2016.02); *A61B 10/0233* (2013.01); *A61B 17/3403* (2013.01);
(Continued)

(58) Field of Classification Search
CPC ...... A61B 17/3403; A61B 2017/00796; A61B 2017/008; A61B 2017/3405;
(Continued)

(56) References Cited

U.S. PATENT DOCUMENTS 5,800,483 A * 9/1998 Vought ..................... A61F 7/00
128/849
5,941,889 A 8/1999 Cermak
(Continued)

FOREIGN PATENT DOCUMENTS

WO 2012112907 A2 8/2012
WO 2015/035249 A2 3/2015
(Continued)

OTHER PUBLICATIONS

International Preliminary Report on Patentability for PCT/US2016/037043 dated Sep. 27, 2016 (5 pages).
(Continued)

*Primary Examiner* — Robert A Lynch
(74) *Attorney, Agent, or Firm* — Brown Rudnick LLP

(57) ABSTRACT

The present disclosure includes customized guidance devices in the form of guidance templates configured to fit over a given area of a patient's body and provide guidance during a tissue treatment or tissue removal procedure of that given area, which may include administration of an agent to a target tissue, target tissue biopsy, target tissue resection, or target tissue ablation. The customized guidance templates are generally constructed via an additive manufacturing process (i.e., three-dimensional (3D) printing) or subtractive manufacturing process (i.e., milling) based on a fabrication instruction file, which may include imaging data of the given area of the patient's body in which targeted tissue treatment is to be performed. The fabrication instruction file may further include additional data, such as the type of procedure to be performed (i.e., biopsy of the tissue abnormality, destruction or resection of the tissue abnormality, etc.).

23 Claims, 17 Drawing Sheets

Related U.S. Application Data

(60) Provisional application No. 62/671,609, filed on May 15, 2018.

(51) Int. Cl.
   *A61B 17/34* (2006.01)
   *A61B 10/02* (2006.01)
   *A61B 17/00* (2006.01)
   *A61B 34/10* (2016.01)
   *A61B 90/00* (2016.01)

(52) U.S. Cl.
   CPC .... *A61B 34/20* (2016.02); *A61B 2017/00796* (2013.01); *A61B 2017/3405* (2013.01); *A61B 2034/107* (2016.02); *A61B 2090/3908* (2016.02)

(58) Field of Classification Search
   CPC .... A61B 2017/3407; A61B 2017/3409; A61B 2017/3411; A61B 34/10; A61B 34/20; A61B 2034/105; A61B 2034/107; A61B 2034/108; A61B 2034/2046; A61B 2034/2065; A61B 2034/2068; A61B 2090/3908; A61B 2090/395; A61B 90/10; A61B 90/11; A61B 90/14; A61B 90/17; A61L 334/10; A61L 334/20
   See application file for complete search history.

(56) References Cited

U.S. PATENT DOCUMENTS

| | | | |
|---|---|---|---|
| 6,128,523 A | | 10/2000 | Bechtold et al. |
| 6,146,377 A | * | 11/2000 | Lee ..................... A61B 8/0825 600/414 |
| 6,304,770 B1 | | 10/2001 | Lee et al. |
| 7,828,744 B2 | | 11/2010 | Rioux et al. |
| 2004/0267121 A1 | | 12/2004 | Sarvazyan et al. |
| 2009/0054757 A1 | | 2/2009 | Noras |
| 2009/0171219 A1 | | 7/2009 | Uchibori |
| 2013/0279782 A1 | | 10/2013 | Trumer et al. |
| 2013/0338479 A1 | | 12/2013 | Pogue et al. |
| 2014/0044333 A1 | | 2/2014 | Barth, Jr. et al. |
| 2014/0142426 A1 | | 5/2014 | Razzaque et al. |
| 2014/0200445 A1 | | 7/2014 | Boezaart et al. |
| 2014/0343404 A1 | | 11/2014 | Razzaque et al. |
| 2015/0150460 A1 | | 6/2015 | Krishnaswamy et al. |
| 2015/0164426 A1 | | 6/2015 | Goossen et al. |
| 2016/0038252 A1 | | 2/2016 | Barth, Jr. et al. |

FOREIGN PATENT DOCUMENTS

| | | |
|---|---|---|
| WO | 2016201341 A1 | 12/2016 |
| WO | 2018/022979 A1 | 2/2018 |

OTHER PUBLICATIONS

International Search Report and Written Opinion for PCT/US2016/037043 dated Sep. 27, 2016 (6 pages).
Invitation to Pay Additional Fees for PCT/US19/29708 mailed Jun. 26, 2019 (2 pages).
International Search Report and Written Opinion for PCT/US2019/029708 dated Aug. 27, 2019 (14 pages).
International Search Report and Written Opinion for PCT/US2019/027315 dated Aug. 9, 2019 (11 pages).

\* cited by examiner

DEVICES FOR GUIDING TISSUE TREATMENT AND/OR TISSUE REMOVAL PROCEDURES

CROSS-REFERENCE TO RELATED APPLICATIONS

This application is a continuation of PCT/US2019/029708, filed Apr. 29, 2019, which claims the benefit of and priority to U.S. Provisional Application Ser. No. 62/671,609, filed May 15, 2018, the contents of which are incorporated by reference in their entirety.

GOVERNMENT RIGHTS

This invention was made with Government support under NIH Grant No. R44CA210810 awarded by the National Cancer Institute under the National Institutes of Health. The Government has certain rights in this invention.

FIELD

The present disclosure relates generally to devices for assisting in medical procedures, and, more particularly, to customized guidance devices in the form of guidance templates configured to fit over a given area of a patient's body and provide guidance for targeted tissue removal or treatment in that given area.

BACKGROUND

Most tissue treatment and/or removal procedures require a high degree of precision so as to ensure the procedure is successful. For example, cancer-related tissue removal procedures generally require a particularly high-degree of accuracy. Cancer is a group of diseases involving abnormal cell growth with the potential to invade or spread to other parts of the body. Cancer generally manifests into abnormal growths of tissue in the form of a tumor that may be localized to a particular area of a patient's body (e.g., associated with a specific body part or organ) or may be spread throughout. Tumors, both benign and malignant, are commonly treated and removed via surgical intervention, as surgery often offers the greatest chance for complete removal and cure, especially if the cancer has not spread to other parts of the body.

Tissue treatment and/or removal procedures are frequently assisted by navigation technology to guide the procedure in real time, wherein such navigation technology typically includes diagnostic imaging systems such as an ultrasound, x-ray, magnetic resonance imaging (MRI), positron emission tomography (PET), computed tomography (CT), thermal, and the like. For example, in the instance of performing a biopsy of a tissue abnormality suspected of being cancerous, such a biopsy may be guided by ultrasound imaging to ensure that the biopsy is performed at the required location.

When performing a biopsy of tissue suspected to be cancerous, proper diagnosis relies on a sample retrieval from a tissue abnormality suspected of being cancerous, not from nearby normal tissues. Thus, it is imperative that a surgeon have proper guidance when performing the biopsy to thereby ensure that the surgeon engages the target tissue and not surrounding healthy tissue, which may otherwise lead to an incorrect negative test result. Furthermore, when surgically destroying or removing a tissue abnormality suspected of being cancerous (or positively identified as cancerous), any cancerous tissue inadvertently left behind may be detrimental to the patient, as reoccurrence of a tumor may most likely occur as a result of this leftover cancerous tissue.

Treatment of early stage breast cancer, for example, may include electrosurgical methods to destroy abnormal tissue growths, in combination with a diagnostic imaging system. For example, a breast tumor resection procedure may include a wire penetrating the breast to reach the tumor or a radio-opaque clip placed within the tumor. The radio-opaque clip may be placed in the tumor during a biopsy procedure. The wire insertion is guided by imaging, for example ultrasound imaging, MRI, or mammography and an electrosurgical procedure is carried out. With current tissue treatment and/or removal procedures, it can be challenging for the surgeon to locate and destroy all traces of cancerous tissue, including any filaments or fimbriae where a reoccurrence of the tumor may most likely occur.

For example, while a typical skilled practitioner can detect tumors and micro-calcifications by ultrasound, available navigation systems may still rely upon free hand positioning, in which operative components of the biopsy or tissue resection system (i.e. the ultrasound transducer wand and the biopsy or electrosurgical device) are each manipulated freely by hand. In other words, the surgeon must employ both hands continuously, and in concert, throughout the procedure, which can have significant drawbacks. For example, a surgeon must concurrently operate the ultrasound transducer wand and position/operate the biopsy or electrosurgical device while watching an image of the working end of the device in relation to the target tissue, which can lead to frustration and/or fatigue for the operator due to the trial and error process of properly aligning the working end of the device and the target tissue. Furthermore, because breast tissue is relatively pliant, manipulation in the form of contact from the biopsy or electrosurgical apparatus and/or the ultrasound transducer may cause the target lesion to move within the breast, and result in an inaccurate penetration of the target tissue (for biopsy purposes) or incomplete destruction or removal of the target tissue.

SUMMARY

The present disclosure is directed to customized guidance devices in the form of guidance templates configured to fit over a given area of a patient's body and provide guidance for targeted tissue treatment or removal in that given area. The customized guidance templates are generally constructed via an additive manufacturing process (i.e., three-dimensional (3D) printing) or subtractive manufacturing process (i.e., milling) based on a fabrication instruction file, which may include imaging data of the given area of the patient's body in which targeted tissue treatment or removal is to be performed. For example, a patient undergoing a breast examination for the detection of breast cancer may generally undergo one or more diagnostic imaging procedures, such as an MRI procedure. The guidance templates of the present disclosure are constructed based, at least in part, on imaging data obtained via such diagnostic imaging procedures. The imaging data may be captured while the patient is in a supine position (i.e., lying horizontally with the face and torso facing up) as most breast cancer diagnostic and treatment procedures are performed in this position. The imaging data may generally include one or more images of one or both breasts (depending whether only one or both breasts are suspected of having a tissue abnormality that could be malignant). The one or more images may include a 3D image, for example, wherein the 3D image may include surface data related to a surface contour of the breasts, volumetric data related to a volume of the breast, spatial properties of the tissue abnormality (i.e., tumor) within the breast, as well as the position of the tissue abnormality within the breast. The fabrication instruction file may further include additional data, such as the type of procedure to be performed (i.e., biopsy of the tissue abnormality, destruction or resection of the tissue abnormality, etc.).

A custom guidance template specific to a given patient's anatomy is constructed from the fabrication file, wherein the guidance template is configured to provide guidance for a procedure to be performed. For example, for a patient undergoing a breast tissue abnormality biopsy or destruction/removal procedure, the guidance template is constructed from a fabrication instruction file having imaging data related to one or more of the patient's breasts. For example, the guidance template may provide unilateral or bilateral cover (i.e., the guidance template may be designed to fit over a single breast or may be designed to fit over both breasts). The guidance template is custom made with specifications based on the imaging data, wherein the guidance template includes cover portion shaped and sized to fit over one or both breasts without compressing or deforming the breasts, the cover portion including an inner surface having a shape, size, and contour that generally matches the shape, size, and contour of the patient's breasts. For example, by utilizing imaging data corresponding to a breast resting in a natural state, such as when the patient is lying in a supine position without any compression upon the breast, the cover may be a reasonable recreation of the breast's form when resting in such a natural state. However, it should be noted that the imaging data may correspond to a breast that has been manipulated during the imaging process. For example, a patient's breast may be intentionally shaped in one way or another during an imaging procedure (i.e., compressed or deformed so as to better capture the identified tissue abnormality in the breast tissue). Accordingly, the cover may include a shape or form corresponding to the imaging data of the manipulated breast, such that, upon placement of the cover over the breast, the cover may apply specific compression or deformation upon the breast so as to recreate the shape of the breast at the time of the imaging procedure.

The guidance template further includes one or more guidance members integrally formed with the cover portion (i.e., 3D printed as a single unitary piece) and configured to guide the specific procedure to be performed. More specifically, the one or more guidance members may include one or more access sites positioned on the guidance template for guiding the working end of a handheld biopsy, injection, or surgical device (i.e., needle, blade, cauterizing tip or ring, ablation tip or electrodes, etc.) into the breast tissue and into contact with the tissue abnormality. The one or more guidance members may further include a fixture or jig positioned relative to the one or more access sites, or to a separately associated site on the guidance template, and configured to retain and control the location and/or motion of the biopsy or surgical device, or an additional device required to complete the procedure, which may include an imaging device such as an ultrasound transducer wand.

In some embodiments, a guidance template consistent with the present disclosure may include a means for maintaining a temperature of nearby breast tissue or skin surface during a procedure involving application of thermal energy (i.e., an ablation procedure), so as to prevent damage to the nearby tissue or skin surface. For example, the guidance template may include a chamber, or series of chambers, within the cover, wherein the chamber is configured to receive a stream of recirculating coolant fluid (i.e., air, liquid, etc.) acting as a coolant flowing from an inlet to an outlet integrally formed with the guidance template and configured to draw any heat from a portion of the breasts. For example, in one embodiment, the guidance template may be include a single chamber generally extending between the interior and exterior surface of the cover and across a majority of the cover, such that excess heat, which may occur as a result of ablation of target tissue in a specific location within the breast, will be drawn away and burning of the surrounding tissue and/or skin surface is prevented. In other embodiments, the guidance template may include a plurality of chambers throughout the cover. In the instance that the specific procedure involves application of thermal energy in a confined region of the breast, the guidance template may simply include a single tube integrally formed with the guidance template and including an inlet and an outlet at either end, wherein the single tube may be arranged about the region in which the procedure is to be performed. For example, the tubing may simply circumscribe an access site, such that, the temperature of any breast tissue or skin surface adjacent the access site will be maintained.

Accordingly, a surgeon need only position the guidance template upon a patient's breasts and utilize the one or more guidance members for carrying out the procedure with a high-degree of accuracy. For example, the one or more access sites are positioned in precise locations upon the guidance template, as dictated by the imaging data, and designed such that a surgeon need only slide a working end therethrough and the access sites will simply guide the working end of the biopsy, injection, or surgical device to the desired target tissue. The inclusion of the biopsy, injection, or surgical device within the fixture or jig greatly improves control over the location and motion of such devices during the procedure, thereby preventing any unnecessary movement and potential disturbance upon the patient's breast during the procedure, including unnecessary contact with the breast, which could otherwise lead to deformation of the breast and movement of the target tissue out of alignment with the access sites. Furthermore, a surgeon may utilize the fixture or jig to hold a handheld portion of an imaging device (e.g., ultrasound transducer wand) in a position relative to the tissue abnormality, while still allowing for rotation of the wand so as to provide a surgeon with a view of the procedure (i.e., view of the working end of the biopsy, injection, or surgical device relative to the target tissue). As such, the guidance template of the present invention greatly improves the outcome of procedures, particularly those requiring a high degree of precision.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

Figure 1:
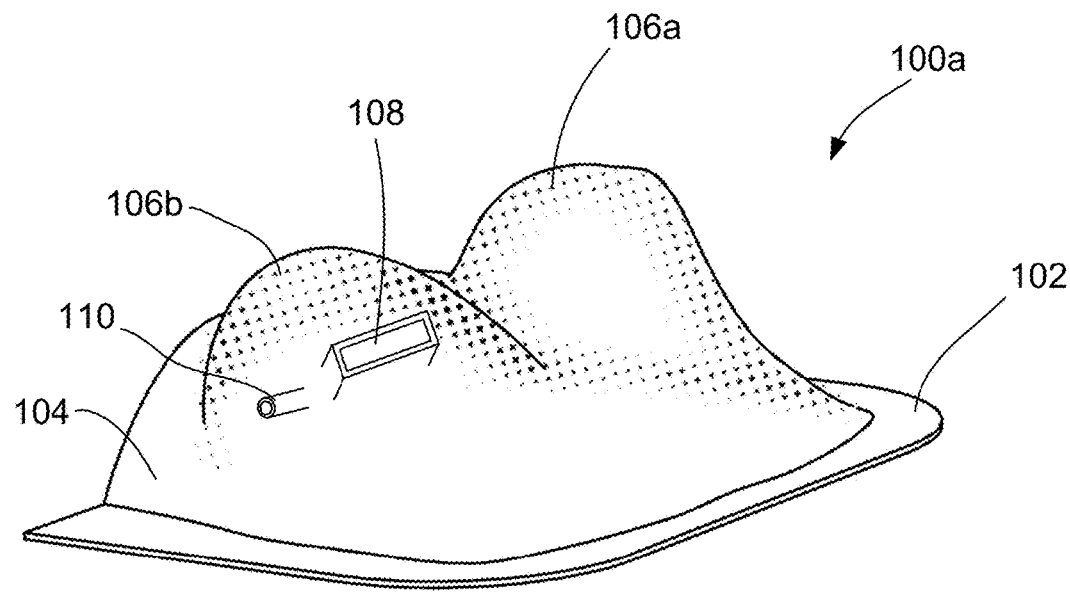
FIG. 1 is a top perspective view of one embodiment of a guidance template consistent with the present disclosure, illustrating guidance members integrally formed with the cover of the guidance template.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

The present disclosure is directed to customized guidance devices in the form of guidance templates configured to fit over a given area of a patient's body and provide guidance for targeted tissue treatment or removal in that given area. The customized guidance templates are generally constructed via an additive manufacturing process (i.e., three-dimensional (3D) printing) or subtractive manufacturing process (i.e., milling) based on a fabrication instruction file, which may include imaging data of the given area of the patient's body in which targeted tissue treatment or removal is to be performed. For example, a patient undergoing a breast examination for the detection of breast cancer may generally undergo one or more diagnostic imaging procedures, such as an MRI procedure. The guidance templates of the present disclosure are constructed based, at least in part, on imaging data obtained via such diagnostic imaging procedures. The imaging data is captured while the patient is in a supine position (i.e., lying horizontally with the face and torso facing up) as most breast cancer diagnostic and treatment procedures are performed in this position. The imaging data may generally include a 3D image of one or both breasts, wherein the 3D image may include surface data related to a surface contour of the breasts, volumetric data related to a volume of the breast, spatial properties of the tissue abnormality (i.e., tumor) within the breast, as well as the position of the tissue abnormality within the breast. The fabrication instruction file may further include additional data, such as the type of procedure to be performed (i.e., biopsy of the tissue abnormality, destruction or resection of the tissue abnormality, etc.).

It should be noted that the customized guidance templates are not limited to fitting breasts for the subsequent guidance of breast-related tissue treatment or removal procedures. Rather, customized guidance templates consistent with the present disclosure can be constructed to fit other given areas of a patient's body in which a targeted tissue, organ, or the like, resides and requires treatment or removal. For example, guidance templates consistent with the present disclosure may be constructed to fit over other portions of the torso (i.e., the abdomen, the upper chest, etc.) or limbs, or the head. However, for sake of clarity and ease of description, the following relates to guidance templates constructed to fit over one or more breasts and to guide a procedure for treating or removing a targeted tissue within said one or more breasts.

Figure 2:
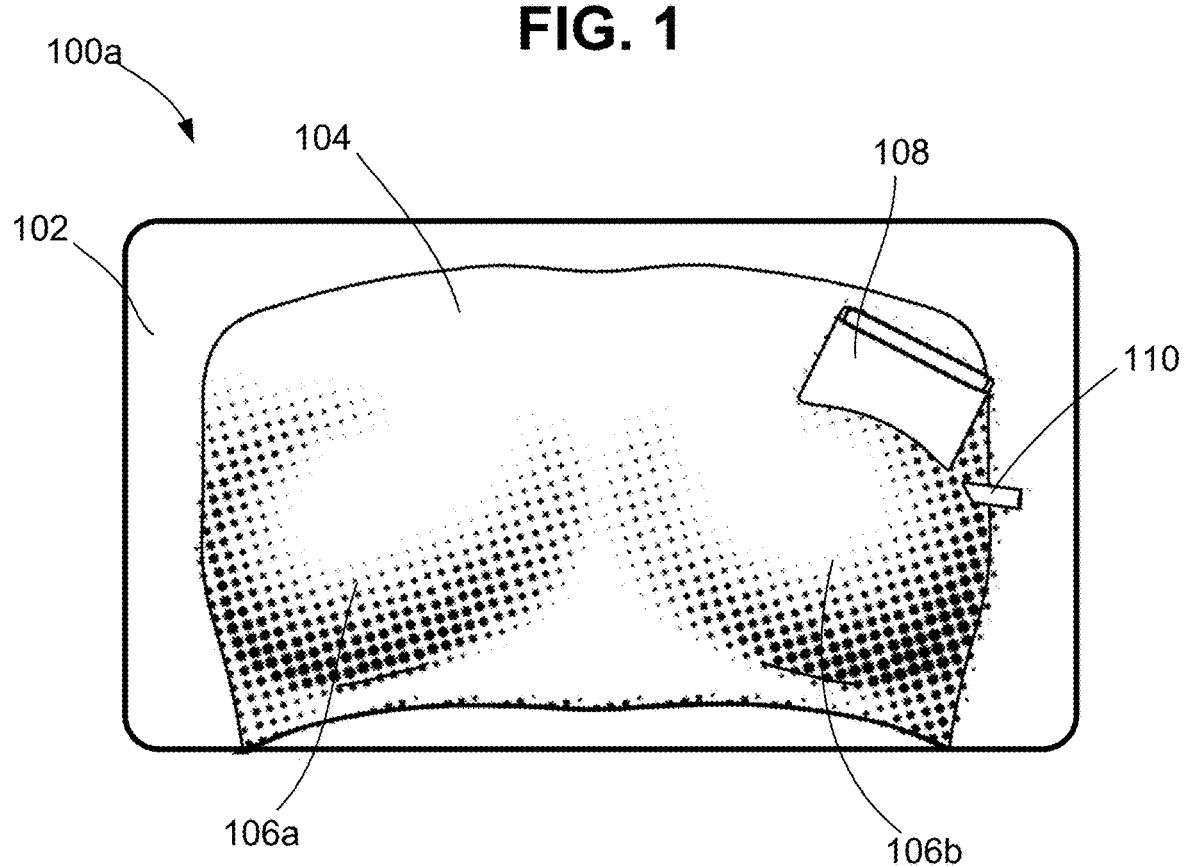
FIG. 2 is a front perspective view of the guidance template of FIG. 1.

FIG. 1 is a top perspective view of one embodiment of a guidance template 100a consistent with the present disclosure. FIG. 2 is a front perspective view of the guidance template 100a. As previously described, the guidance template 100a is customized to a specific portion of a patient's anatomy and will guide a tissue treatment or removal procedure within that area. For example, as shown in the figures, the guidance template 100a is formed so as to match a patient's breast and is configured to guide a breast tissue biopsy. For example, for a patient undergoing a breast tissue abnormality biopsy or destruction/removal procedure, the guidance template 100a is constructed from a fabrication instruction file having imaging data related to the patient's breasts. As such, the guidance template 100a is custom made with specifications based on the imaging data. It should be noted that, while the guidance template of FIG. 1 is illustrated as covering a pair of breasts, guidance templates consistent with the present disclosure may be unilateral or bilateral. In particular, in most cases, only a single breast will be undergoing a tissue treatment and/or tissue removal procedure. As such, a guidance template consistent with the present disclosure may be designed to fit over a single breast, as opposed to fitting over both breasts. However, as shown in a majority of figures herein, the guidance template may be designed to fit over bother breasts.

As shown, the guidance template 100a may include a base portion 102 generally configured to rest upon the patient's torso area immediately surrounding the breasts (i.e., the upper chest, ribs, upper abdomen areas). However, it should be noted that some embodiments may be devoid of a base portion 102. The guidance template 100a further includes a cover portion 104 shaped and sized to fit over the breasts without compressing or deforming the breasts. As shown, the cover portion 104 includes a pair of breast forms 106a, 106b matching the patient's breasts (shown in FIGS. 3A, 3B, and 4). In particular, the breast forms 106a, and 106b each include an inner surface having a shape, size, and contour that matches the shape, size, and contour of the corresponding breast, as based on imaging data used in constructing the cover 104.

For example, the customized guidance template 100a is generally constructed via an additive manufacturing process (i.e., three-dimensional (3D) printing) or subtractive manufacturing process (i.e., milling) based on a fabrication instruction file, which may include imaging data of one or both of the patient's breast (i.e., a unilateral or bilateral coverage), wherein such imaging data is obtained via one or more diagnostic imaging procedures. For example, a guidance template may be constructed from one or more image sets, which may include, for example, a contrast MRI sequence and a large field view structure/anatomy sequence, or a set of two co-acquired/co-registered image sets from different modalities. The guidance template is custom made with specifications based on the imaging data, such that the cover portion 104 may include an inner surface having a shape, size, and contour that generally matches the shape, size, and contour of one or both of the patient's breasts depending on the procedure to be performed.

Figure 3A:
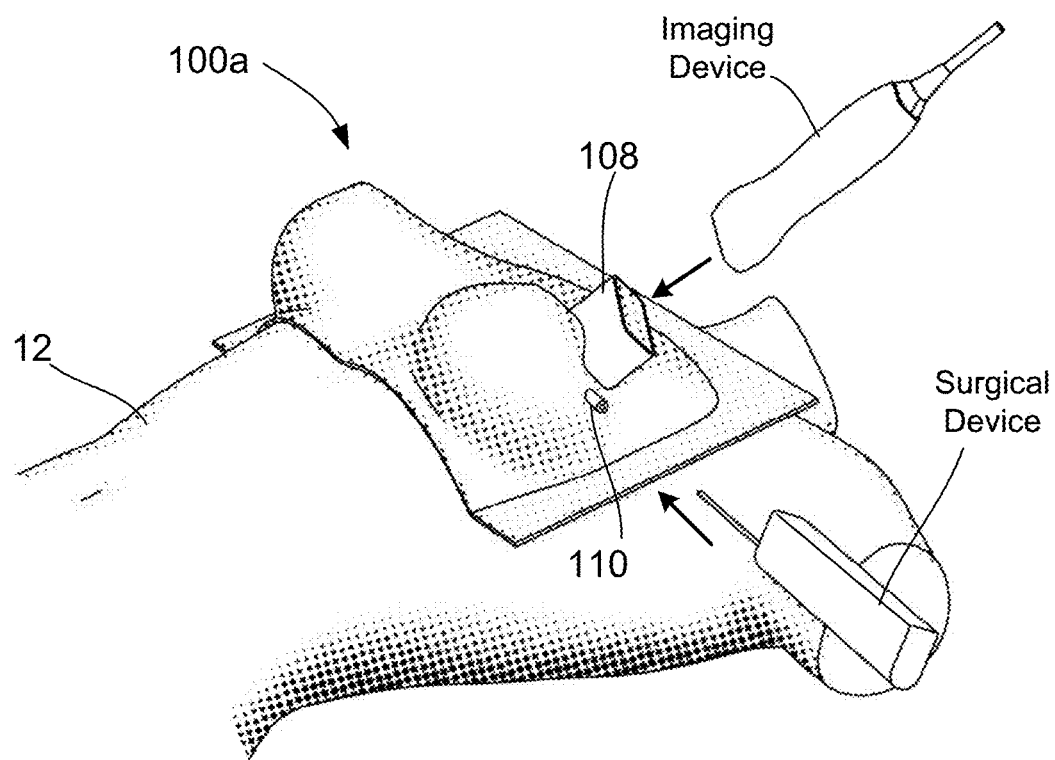
FIG. 3A is a side perspective view of the guidance template of FIG. 1 positioned upon a patient's chest laying in a supine position and illustrating alignment of a surgical device (i.e., biopsy device) and a handheld imaging device (i.e., ultrasound transducer wand) with associated guidance members integrally formed with the cover of the guidance template.
Figure 3B:
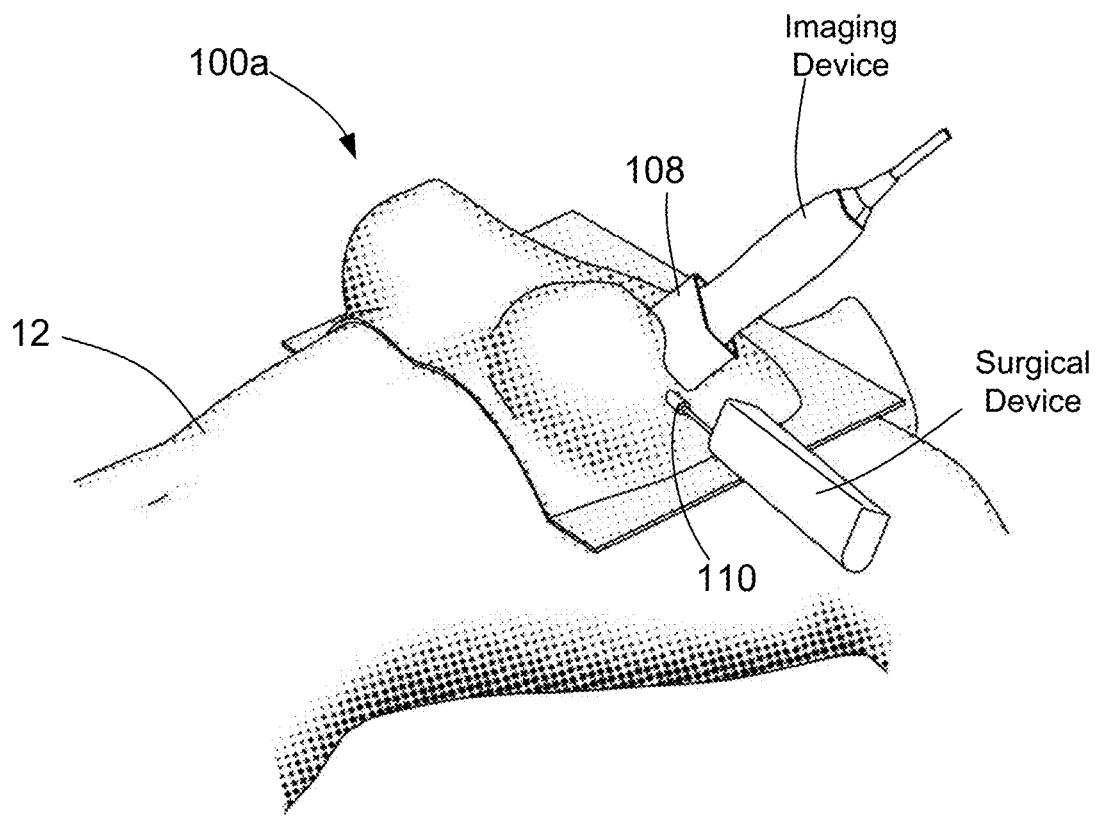
FIG. 3B is a side perspective view of the guidance template of FIG. 1 positioned upon a patient's chest and illustrating positioning and coupling, respectively, of the working end surgical device (i.e., biopsy device) within the associated guidance member and the handheld imaging device (i.e., ultrasound transducer wand) to the associated guidance member.
Figure 4:
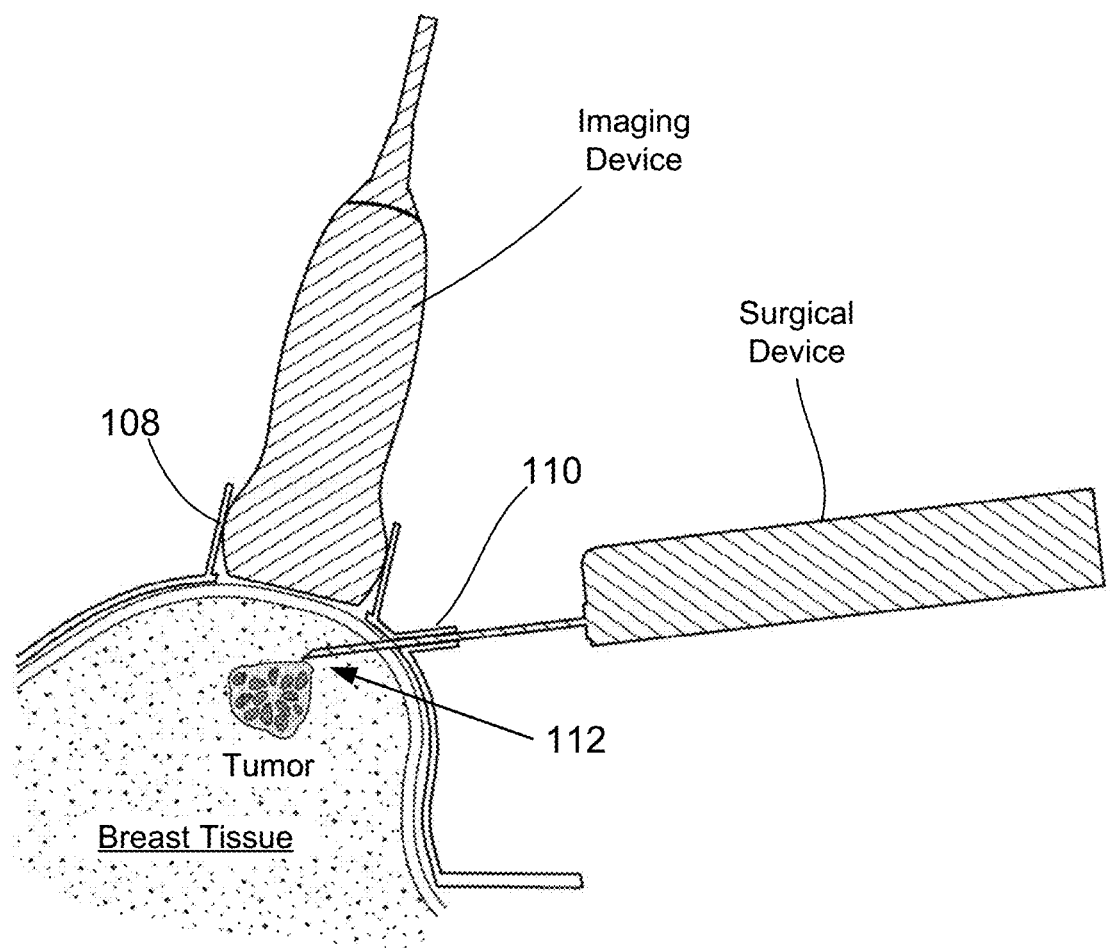
FIG. 4 is a cross-sectional view of FIG. 3B illustrating positioning of the working end of a biopsy device (i.e., the needle) within the breast tissue and towards a tumor, as guided by the associated access site through which the needle extends and further illustrating coupling of the ultrasound transducer wand to a respective jig for controlling position and motion of the wand relative to the breast tissue.

For example, in some embodiments, the imaging data may be captured while the patient is in a supine position (i.e., lying horizontally with the face and torso facing up) as most breast cancer diagnostic and treatment procedures are performed in this position, as shown in FIGS. 3A, 3B, and 4. By utilizing imaging data corresponding to a breast resting in a natural state, such as when the patient is lying in a supine position without any compression upon the breast, the cover may be a reasonable recreation of the breast's form when resting in such a natural state.

The imaging data may generally include at least a 3D image, or images, of one or both breasts, wherein the 3D image may include surface data related to a surface contour of the breasts, volumetric data related to a volume of the breast, spatial properties of the tissue abnormality (i.e., tumor) within the breast, as well as the position of the tissue abnormality within the breast. Systems and methods for obtaining such imaging data and further creating a fabrication instruction file is described in international PCT Publication No. WO/2016/201341, filed Oct. 6, 2016, the entire contents of which are incorporated by reference herein in their entirety. Accordingly, the breast forms 106a, 106b have a precise shape and size the mimics the shape and size of the patient's breasts, thereby providing a precise fitting as intended by the manner in which the breasts were presented during the imaging procedure.

It should be noted that the imaging data may correspond to a breast that has been manipulated during the imaging process. For example, a patient's breast may be intentionally shaped in one way or another during an imaging procedure (i.e., compressed or deformed so as to better capture the identified tissue abnormality in the breast tissue). Accordingly, the cover may include a shape or form corresponding to the imaging data of the manipulated breast, such that, upon placement of the cover over the breast, the cover may apply specific compression or deformation upon the breast so as to recreate the shape of the breast at the time of the imaging procedure.

The fabrication instruction file may further include additional data, such as the type of procedure to be performed (i.e., biopsy of the tissue abnormality, destruction or resection of the tissue abnormality, etc.). Accordingly, the guidance template 100a further includes one or more guidance members integrally formed with the cover portion 104 (i.e., 3D printed as a single unitary piece) and configured to guide the specific procedure to be performed. For example, as shown in the figures, the guidance template 100a may include one or more access sites 110 positioned on the cover portion 104 for guiding the working end of a handheld biopsy, injection, or surgical device (i.e., needle, blade, cauterizing tip or ring, ablation tip or electrodes, etc.) into the breast tissue and into contact with the tissue abnormality (shown in FIGS. 3B and 4). For example the access site 110 may generally include a port providing a channel extending entirely through the cover portion 104 from an exterior surface to an interior surface of the cover portion 104. The guidance template 100a may further include a fixture or jig 108 positioned relative to the one or more access sites 110, or to a separately associated site on the guidance template 100a, and configured to retain and control the location and/or motion of the biopsy or surgical device, or an additional device required to complete the procedure, which may include an imaging device such as an ultrasound transducer wand, as will be described in greater detail herein.

FIGS. 3A and 3B are side perspective views of the guidance template 100a positioned upon a patient 12 laying in a supine position on a table 10. As shown in FIG. 3A, a surgical device (i.e., biopsy device) and a handheld imaging device (i.e., ultrasound transducer wand) are aligned with associated access site 110 and jig 108, respectively. As shown in FIG. 3B, the working end of the biopsy device (i.e., the needle) is positioned within the associated access site 110 and the ultrasound transducer wand is coupled to the associated jig 108. FIG. 4 is a cross-sectional view of FIG. 3B illustrating positioning of the needle of the biopsy device within the breast tissue and towards a tumor (indicated by arrow 112), as guided by the associated access site 110 through which the needle extends, and further illustrates coupling of the ultrasound transducer wand to the respective jig 108 for controlling position and motion of the wand relative to the breast tissue.

A surgeon need only position the guidance template 100a upon a patient's breasts and utilize the access site 110 and jig 108 for carrying out the procedure with a high-degree of accuracy. For example, the access site 110 and the jig 108 are positioned in precise locations upon the cover portion 104, as dictated by the imaging data, and designed such that a surgeon need only slide the needle of the biopsy device into the access site 110, wherein the access site 110 will simply guide the needle tip to the desired target tissue (i.e., the tumor). Furthermore, coupling of the ultrasound transducer wand to the jig 108 improves control over the location and motion of the wand during the procedure. In the illustrated embodiment, the jig 108 may generally resemble a socket configured to receive and provide a friction fit with the wand, thereby substantially immobilizing the working end of the wand in a position close to the breast tissue, while still allowing for some rotational movement of the wand (i.e., rocking motion) so as to provide a surgeon with a view of the procedure (i.e., view of the needle relative to the target tissue). The jig 108 maintains the wand in position relative to the breast to provide a steady viewing plane during insertion of the biopsy needle and further prevents any unnecessary movement and potential disturbance upon the patient's breast during the procedure, including unnecessary contact with the breast, which could otherwise lead to deformation of the breast and movement of the target tissue out of alignment with the access site 110, and thus out of position relative to the needle. As such, the guidance template 100a of the present invention greatly improves the outcome of procedures, particularly those requiring a high degree of precision.

Figure 5:
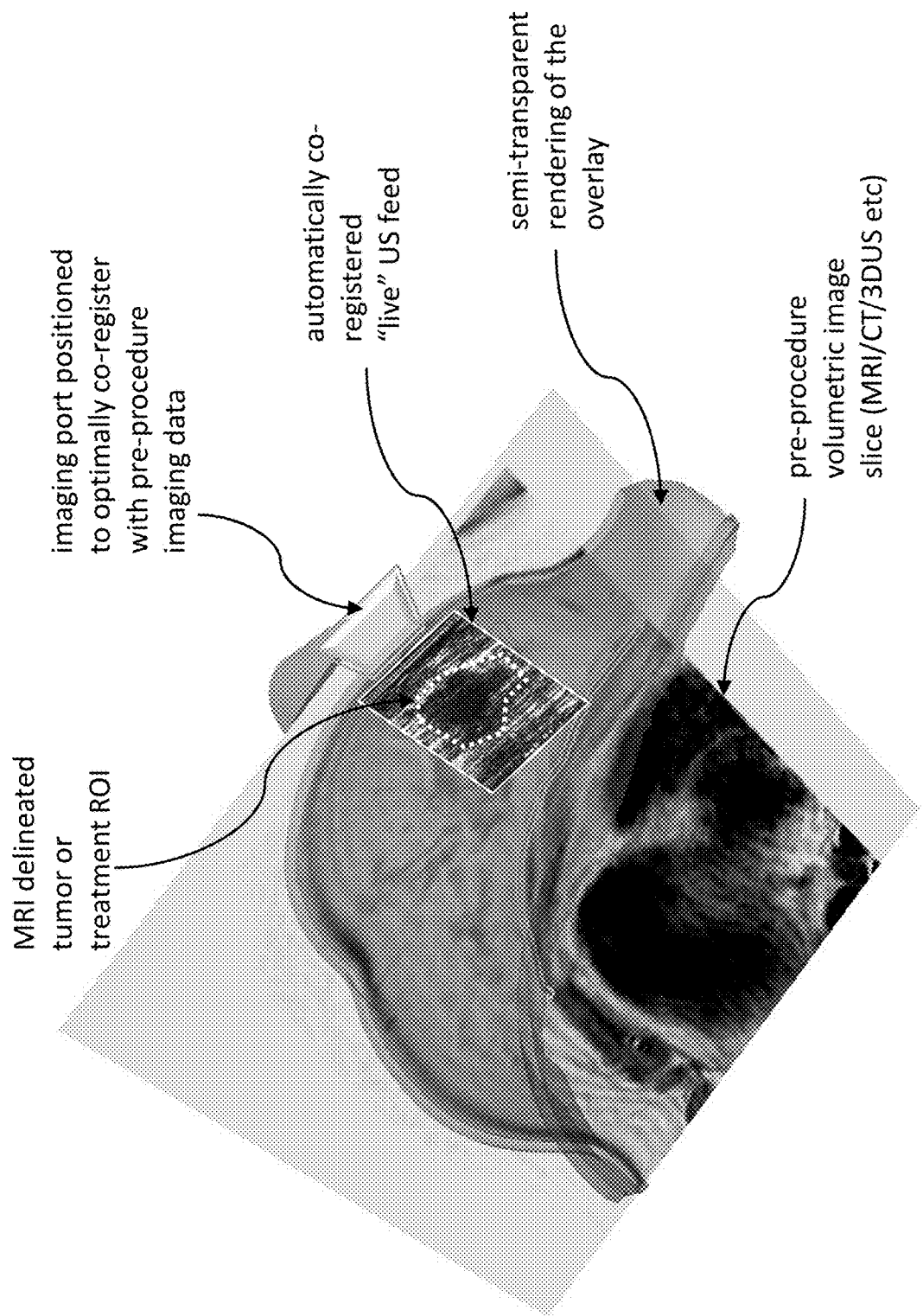
FIG. 5 is a side view illustrating optimized placement of at least one of the access site and jig relative to the target tissue (i.e., tumor)

FIG. 5 is a side view illustrating optimized placement of at least one of the access site 110 and jig 108 relative to the target tissue (i.e., tumor). In some embodiments, the access site 110 and or jig 108 may be constructed on the cover portion 104 in an orientation that generally corresponds to an orientation of the imaging data from which the access site and/or jig are based. For example, the jig 108 which may be used to hold the imaging device (i.e., wand of the ultrasound system) may be oriented so as to match the native MR slice geometry which allows for optimal visualization of the breast tissue and tissue abnormality (i.e., tumor) during a tissue treatment and/or removal procedure utilizing the guidance template 100. For example, the jig 108, which is used generally as an imaging port in the illustrated embodiment, may be located on the cover portion 104 in an optimal position based on pre-op imaging data geometry, such that, during a subsequent procedure, the feedback from the ultrasound (captured via the wand positioned within the jig 108) can be co-registered with the larger field of view pre-op MRI, which may provide a greater overall anatomical context and more complete assessment of the target tissue and surrounding tissue during the procedure.

Figure 6A:
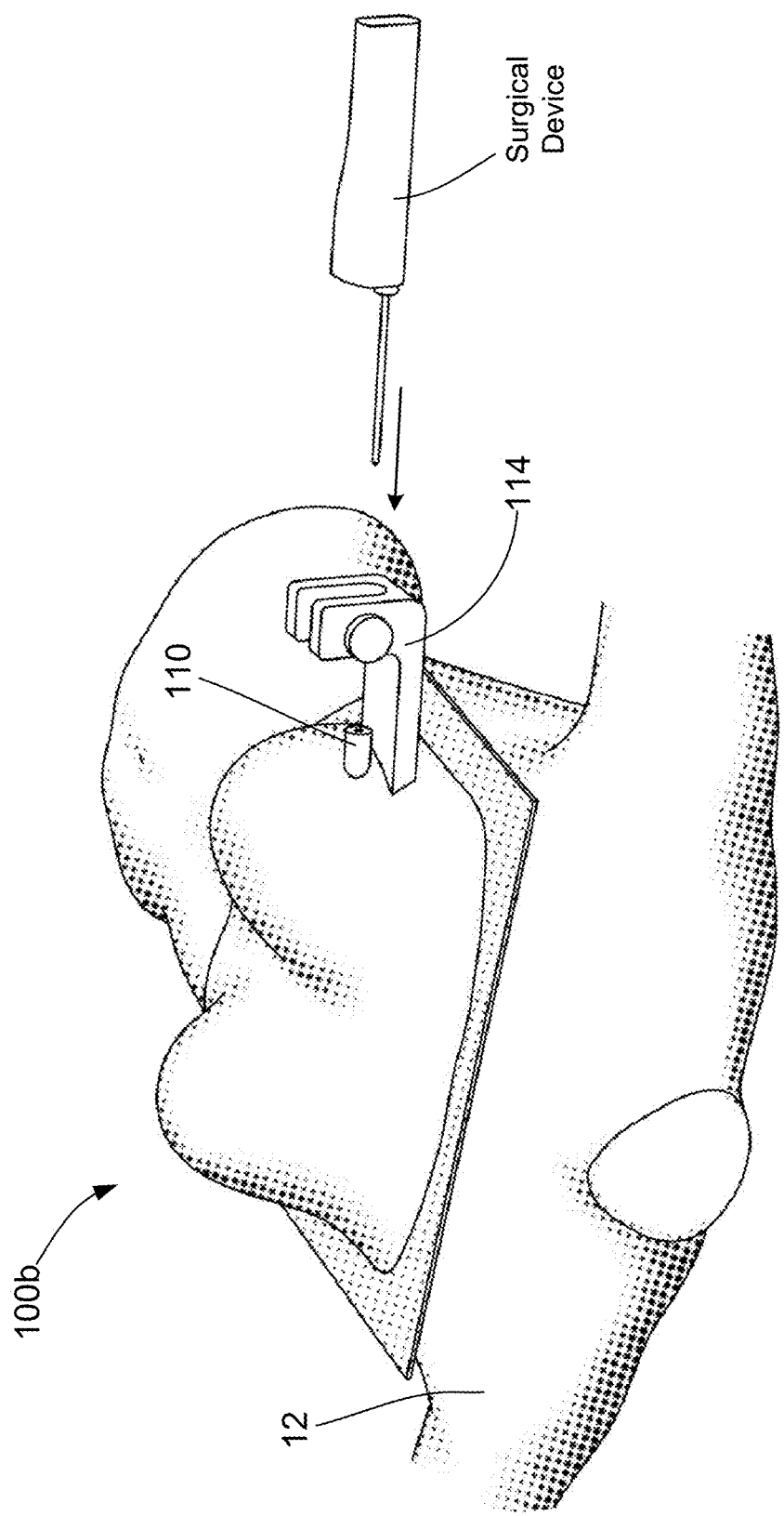
FIG. 6A is top perspective view of another embodiment of a guidance template consistent with the present disclosure, illustrating the guidance template positioned upon a patient's chest and illustrating alignment of a surgical device (i.e., ablation device) with an access site, for receiving and guiding the working end of the surgical device (i.e., ablation element(s)) into the target tissue within the breast, and an associated jig for retaining the surgical device in alignment with the access site.
Figure 6B:
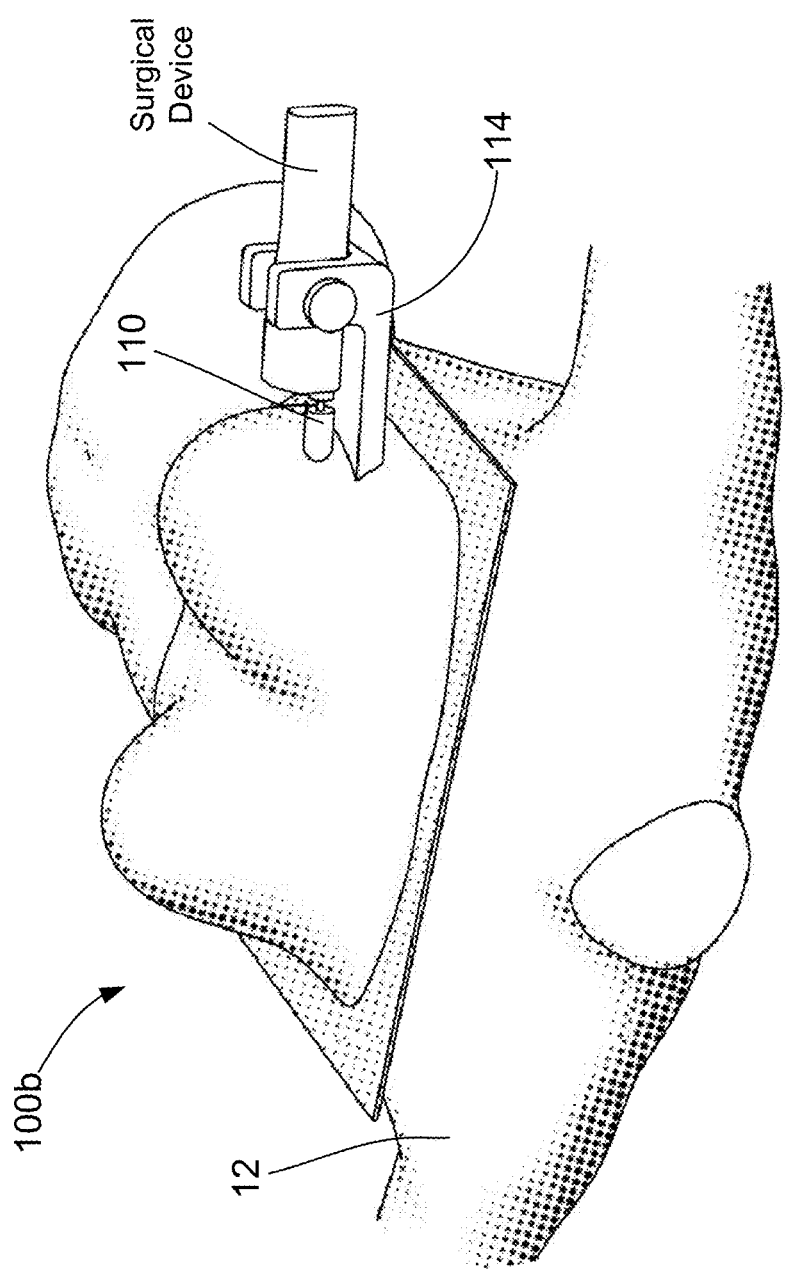
FIG. 6B is a top perspective view of the guidance template of FIG. 6A positioned upon the patient's chest and illustrating coupling of the surgical device (i.e., ablation device) to the jig and subsequent positioning of the working end of the surgical device (i.e., ablation element(s)) through the access site.

FIG. 6A is top perspective view of another embodiment of a guidance template 100b consistent with the present disclosure. Similar to the guidance template 100a of FIGS. 1-4, the guidance template 100b is customized to fit over a patient's breast and includes at least one access site 110 to receive and guide a working end of a surgical device into engagement with a target tissue in the patient's breast(s). In this embodiment, the surgical device may include an ablation device including an ablation element for ablating the target tissue. The guidance template 100b further includes a jig 114 configured for retaining the ablation device in alignment with the access site 110. For example, as shown in FIG. 6B, the jig 114 is aligned with the access site 110, such that, upon coupling the ablation device to the jig 114, the ablation element of the ablation device (an elongate probe including one or more ablation elements at a distal portion thereof) is positioned through the access site 110 and guided to the target tissue, wherein the jig 114 maintains the ablation device in a desired position, thereby relieving the physician of having to hold the ablation device throughout the entire procedure, which could otherwise be tiresome for the surgeon and result in unsteady movement during the procedure.

Figure 7A:
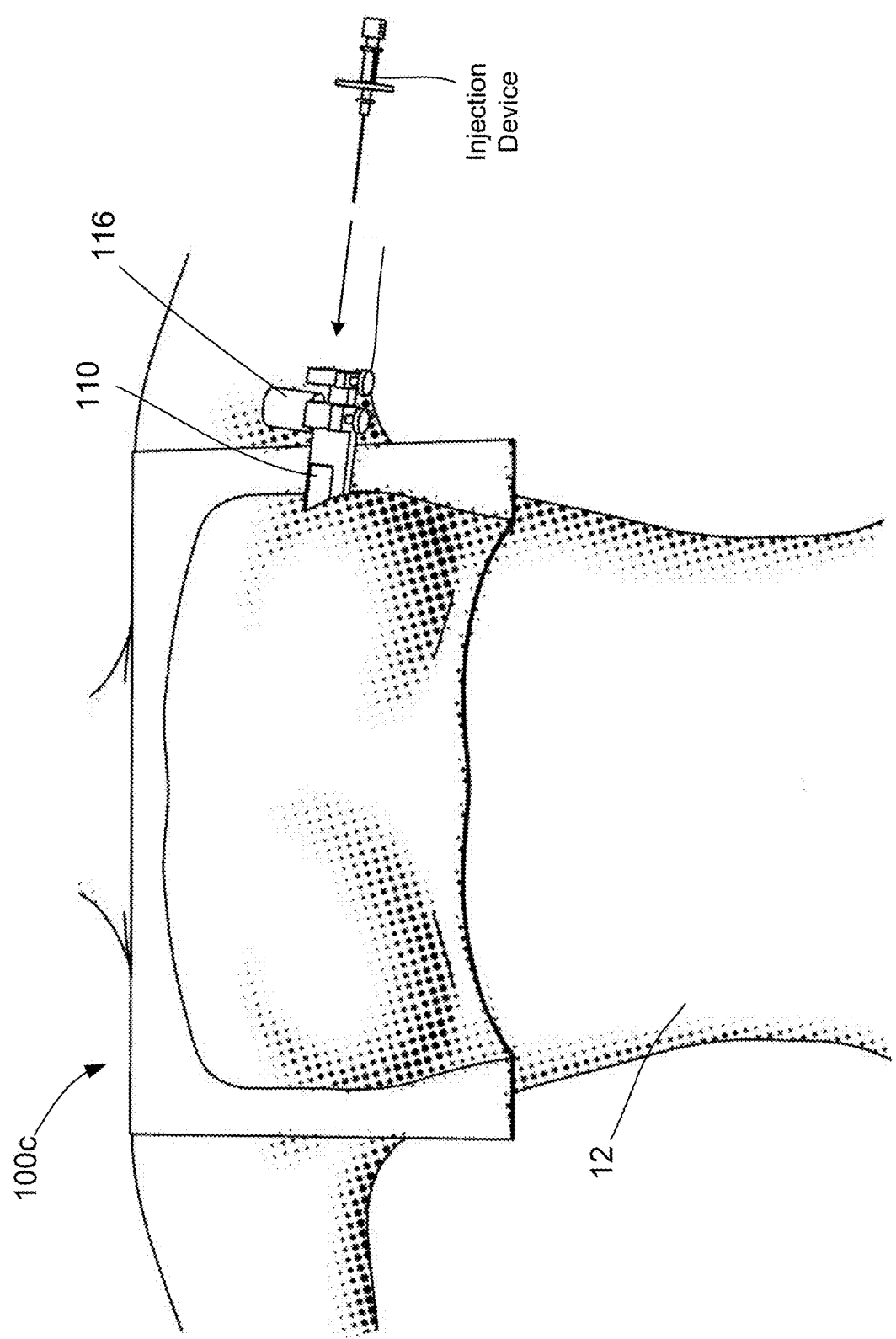
FIG. 7A is top perspective view of another embodiment of a guidance template consistent with the present disclosure, illustrating the guidance template positioned upon a patient's chest and illustrating alignment of an injection device with an access site, for receiving and guiding the working end of the injection device into the target tissue within the breast, and an associated jig for retaining the injection device in alignment with the access site.
Figure 7C:
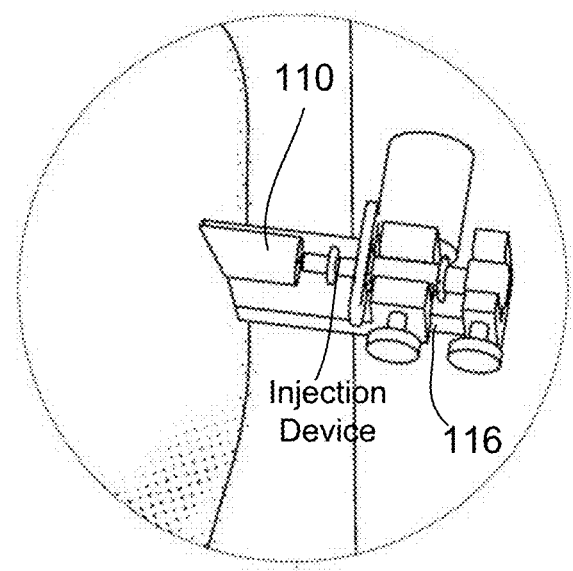
FIG. 7C is an enlarged top perspective view illustrating the coupling of the injection device to the jig in greater detail.
Figure 7B:
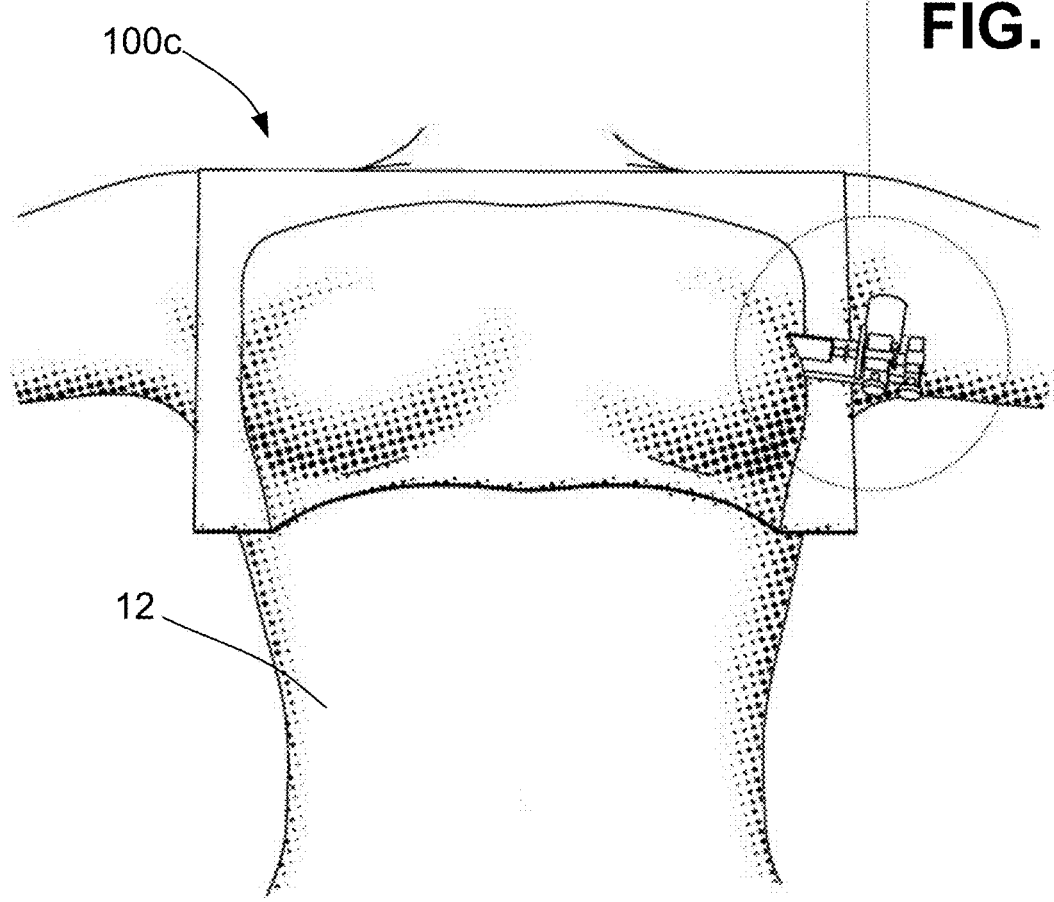
FIG. 7B is a top perspective view of the guidance template of FIG. 7A positioned upon the patient's chest and illustrating coupling of the injection device to the jig and subsequent positioning of the working end of the injection device (i.e., needle) through the access site.

FIG. 7A is top perspective view of another embodiment of a guidance template 100c consistent with the present disclosure. Similar to guidance templates previously described herein, the guidance template 100c is customized to fit over a patient's breast and includes at least one access site 110 to receive and guide a working end of an injection device into engagement with a target tissue in the patient's breast(s). In this embodiment, the injection device may include a syringe including a needle for facilitating delivery of a fluid therapeutic to the target tissue, for example. The guidance template 100c further includes a jig 116 configured for retaining the injection device in alignment with the access site 110. For example, as shown in FIGS. 7B and 7C, the jig 116 is aligned with the access site 110, such that, upon coupling the injection device to the jig 116, the needle is positioned through the access site 110 and guided to the target tissue, wherein the jig 116 maintains the injection device in a desired position, thereby relieving the physician of having to hold the ablation device throughout the entire procedure.

Figure 8:
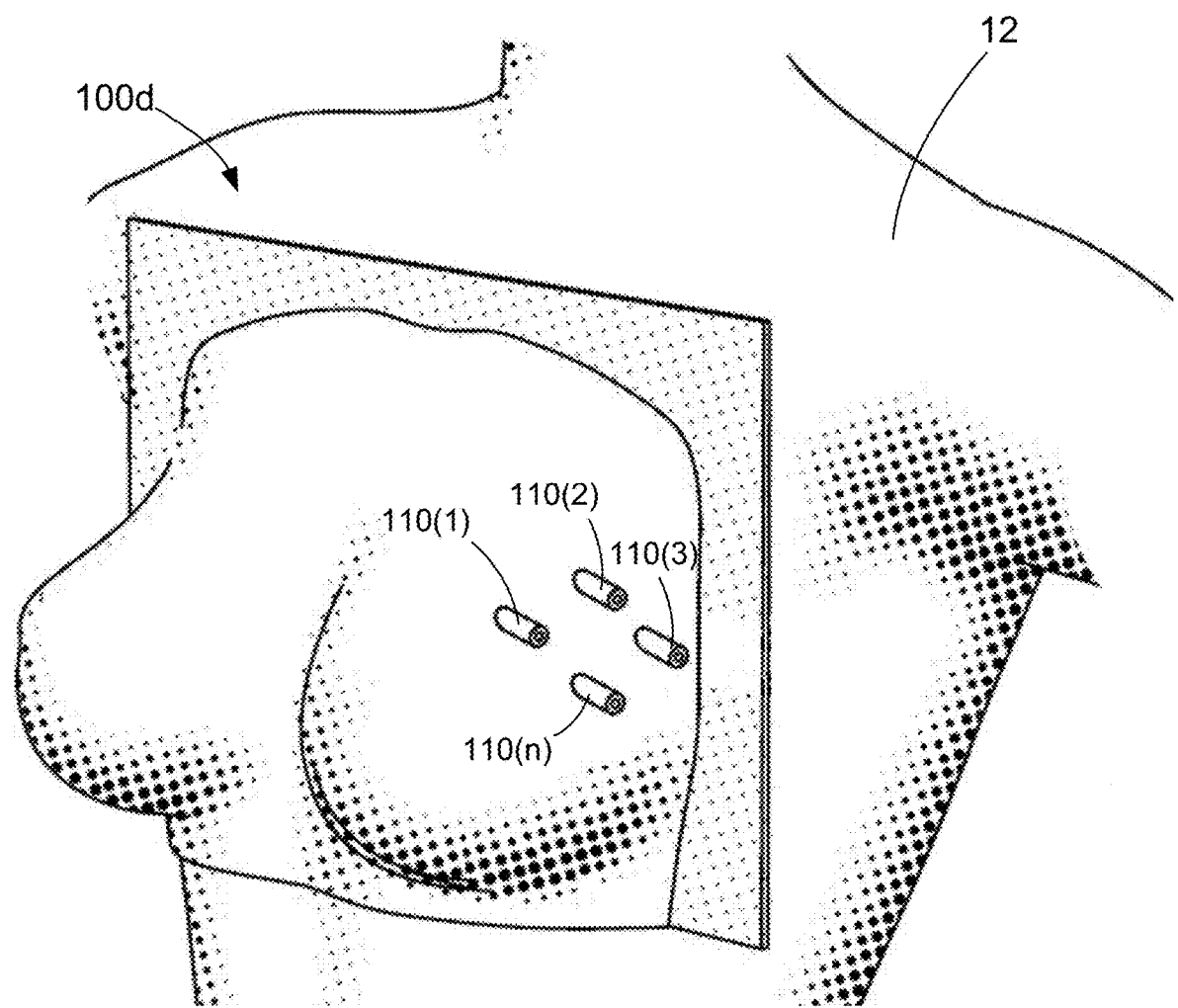
FIG. 8 is a side perspective view of another embodiment of a guidance template consistent with the present disclosure, wherein the guidance template comprises a plurality of access sites patterned about a target tissue site.

FIG. 8 is a side perspective view of another embodiment of a guidance template 100d consistent with the present disclosure. Similar to guidance templates previously described herein, the guidance template 100d is customized to fit over a patient's breast and includes a plurality of access sites 110(1), 110(2), 110(3), and 110(n) to receive and guide a working end of a surgical device into engagement with a target tissue in the patient's breast(s). For example, one type of tissue treatment procedure is referred to as irreversible electroporation (IRE), which is a soft tissue ablation technique using ultra short but strong electrical fields to create permanent and hence lethal nanopores in the cell membrane, to disrupt the cellular homeostasis and eventually resulting in cell death via apoptosis. IRE may be carried out via ablation surrounding the target tissue. The plurality of access sites 110(1)-110(n) are arranged with precise equal spacing, so as to guide ablation probes or needles into the breast tissue and surround the target tissue with precise spacing there between, so as to maintain parallelism, allow for the effective ablation of the target tissue.

Figure 9:
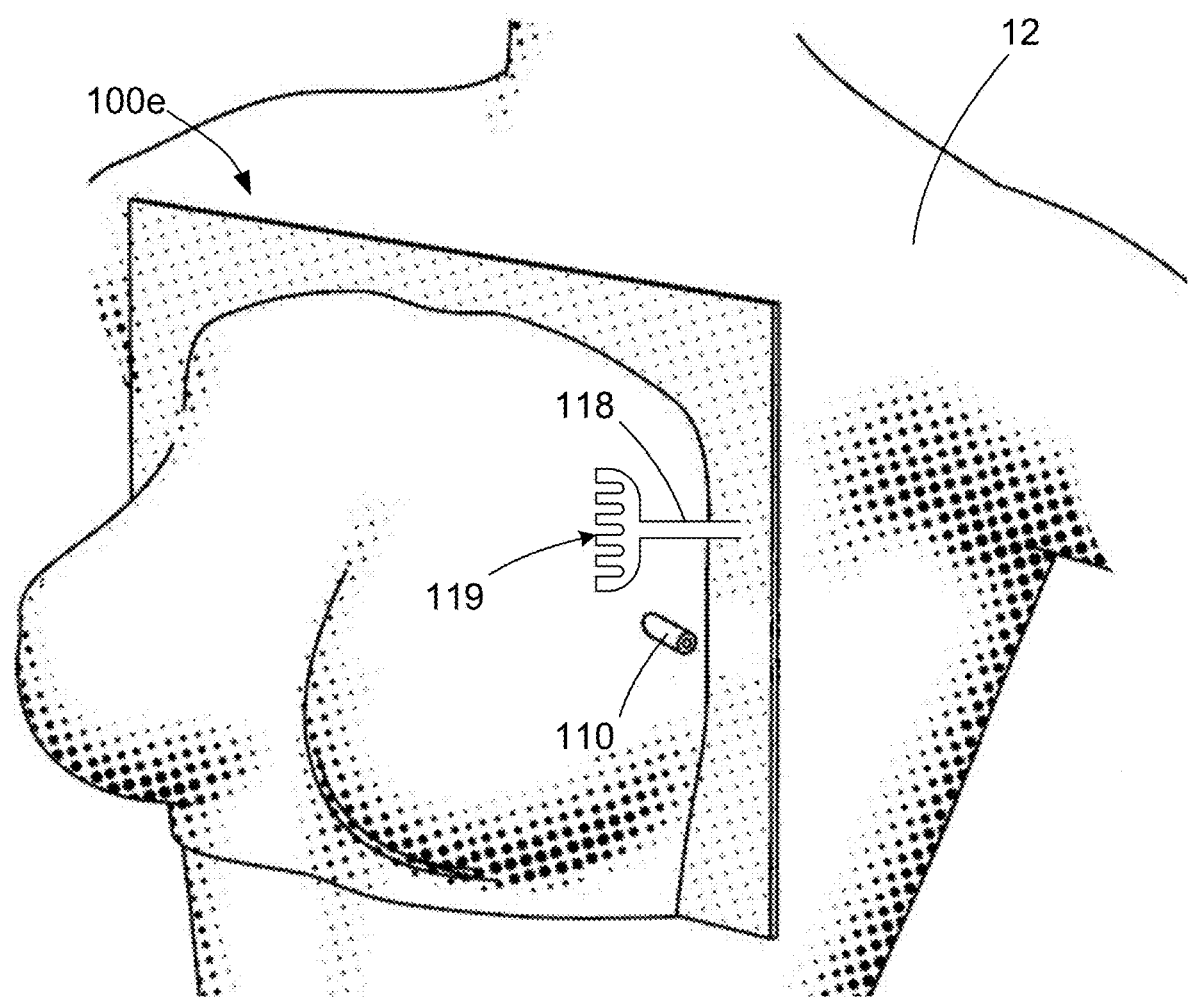
FIG. 9 is a side perspective view of another embodiment of a guidance template consistent with the present disclosure, wherein the guidance template comprises at least one access site and a stand configured to provide cable management (i.e., retain one or more cables connected to respective devices or systems used during a procedure)

FIG. 9 is a side perspective view of another embodiment of a guidance template 100e consistent with the present disclosure. As shown, a guidance template consistent with the present disclosure may include a stand 118 having a distal frame 119 configured to provide cable management. For example, during any given procedure, a plurality of wires and cables (connected to various devices and systems, such as the ablation device, handheld imaging device, etc.) may be present and thus may interfere with the procedure. The distal frame 119 may be configured to retain one or more wires or cables within and may further maintain such wires and cables a safe distance from the working site (i.e., maintain the wires and cables off of the patient and out of the working area). While the cable management assembly (i.e., stand and frame 118, 119) are shown extending from the base 102, it should be noted that the cable management assembly can be constructed on any portion of the guidance template, including the cover portion 104.

Figure 10:
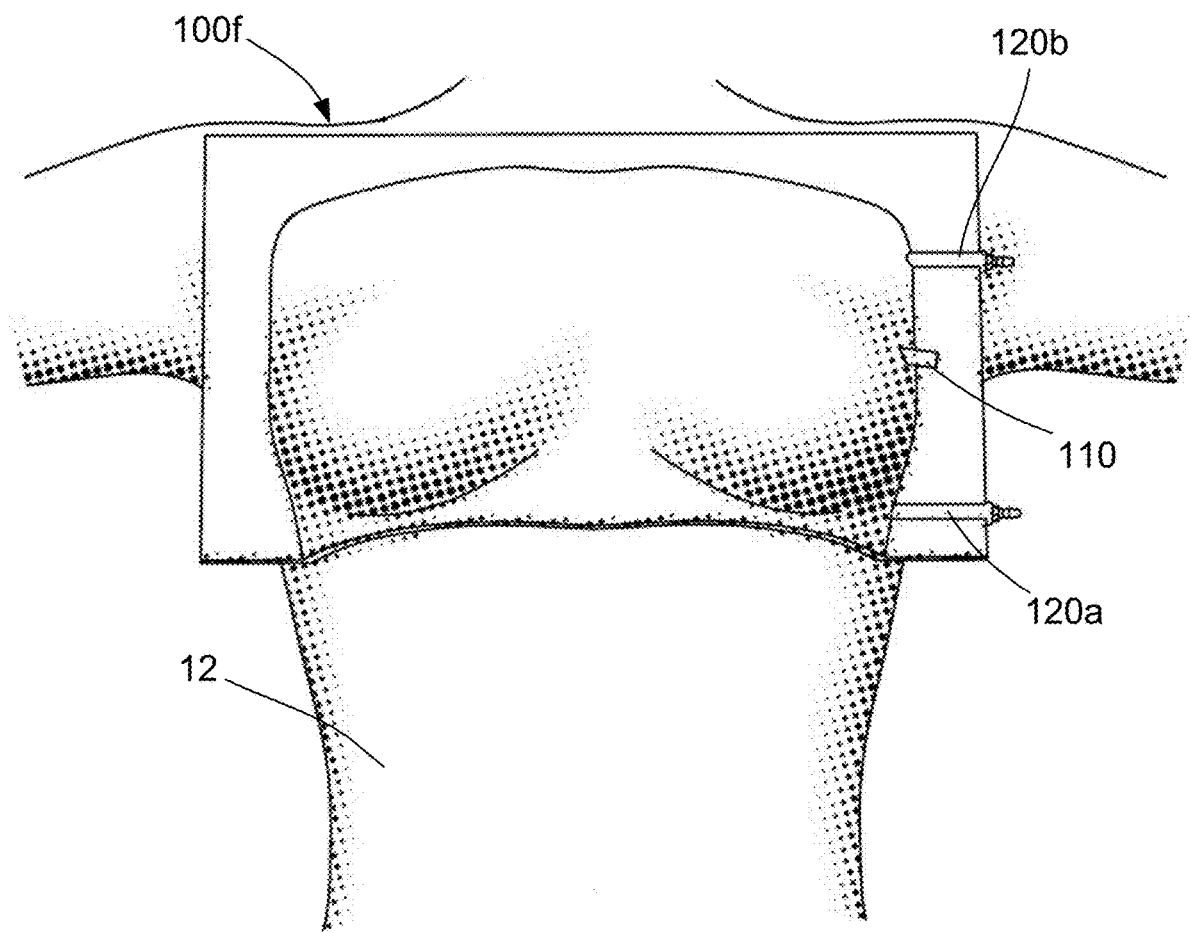
FIG. 10 is a front perspective view of another embodiment of a guidance template consistent with the present disclosure, wherein the guidance template comprises a temperature management assembly.
Figure 11A:
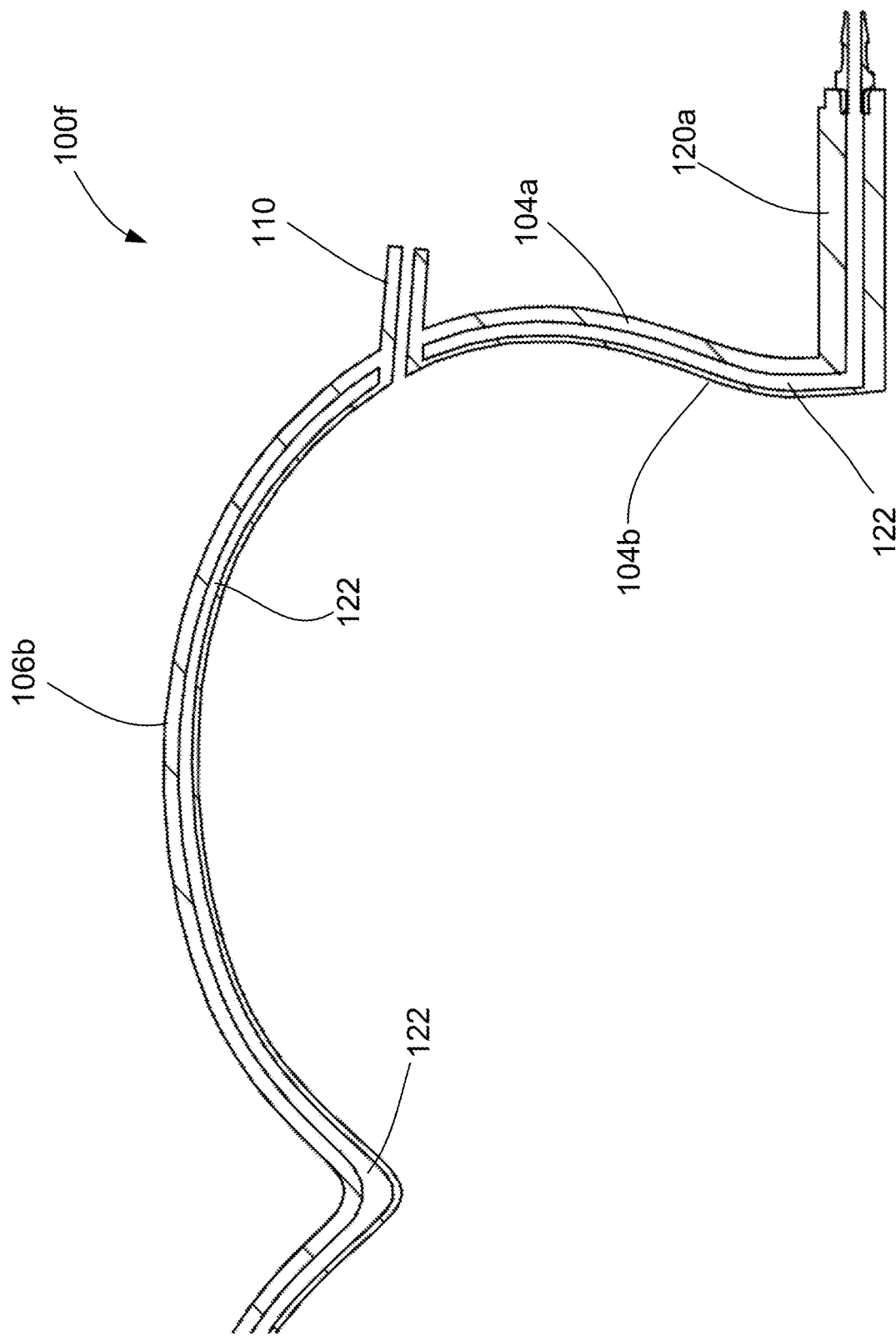
FIG. 11A is a cross-sectional view of the guidance template of FIG. 10 illustrating a chamber of the temperature management assembly and associated inlet and outlet ports allowing for a recirculating coolant fluid to flow through the chamber.

FIG. 10 is a front perspective view of another embodiment of a guidance template 100f consistent with the present disclosure and FIG. 11A is a cross-sectional view of the guidance template 100f. Similar to guidance templates previously described herein, the guidance template 100f is customized to fit over a patient's breast and includes at least one access site 110 to receive and guide a working end of a surgical device into the breast tissue and into engagement with a target tissue. The guidance template 100f further includes a temperature management assembly for maintaining a temperature of nearby breast tissue or skin surface during a procedure involving application of thermal energy (i.e., an ablation procedure), so as to prevent damage to the nearby tissue or skin surface. For example, the temperature management assembly may generally include a chamber 122, or series of chambers, within the cover portion 104, wherein the chamber 122 is configured to receive a stream of recirculating coolant fluid (i.e., air, liquid, etc.) acting as a coolant flowing from an inlet 120a to an outlet 120b integrally formed with the guidance template 100f and configured to draw any heat from a portion of the breasts. As shown in FIG. 11A, for example, the guidance template 100f may be include a single chamber 122 generally extending between the interior surface and exterior surface of the cover portion 104 and across a majority of the cover 104, such that excess heat, which may occur as a result of ablation of target tissue in a specific location within the breast, will be drawn away and burning of the surrounding tissue and/or skin surface is prevented. In some embodiments, the guidance template 100f may be comprised of two plates 104a and 104b coupled to one another and having the chamber 122 formed there between. The inlet 120a and outlet 120b can be connected to standard operating room air or vacuum sources, and liquid cooling can be achieved with a chilled saline bag, for example, via use of a common operating room peristaltic tubing pump.

Figure 11B:
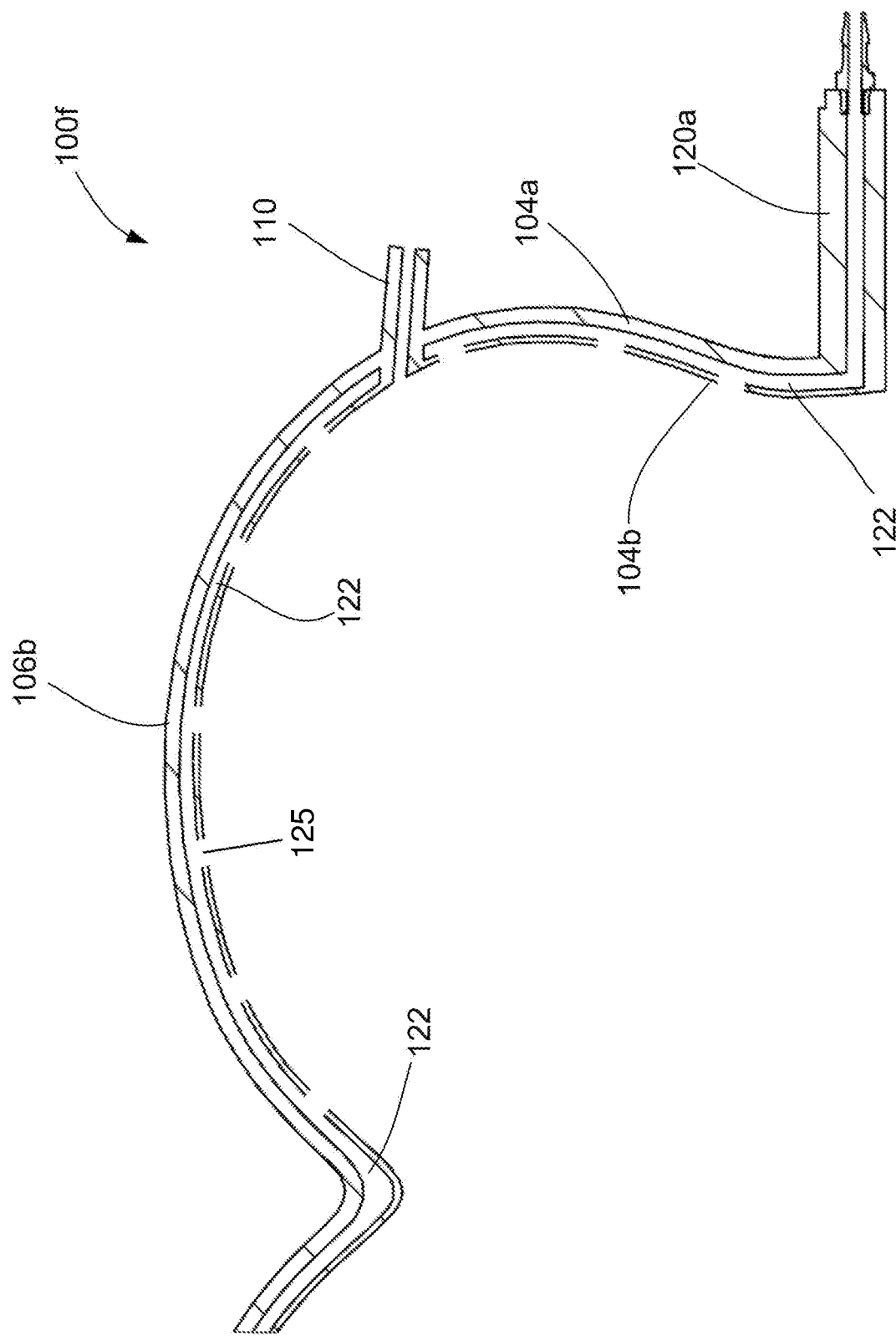
FIG. 11B is a cross-sectional view of another embodiment of the guidance template illustrating a chamber with associated apertures configured to create suction for supporting and stabilizing tissue.

In a related embodiment shown in FIG. 11B, the guidance template 100f includes a suction assembly to allow a patient's tissue to be drawn toward the cover 104 to stabilize the breast during imaging or surgery. The suction assembly includes a plurality of apertures 125 in inner plate 104b. The apertures 125 are in fluid communication with the chamber 122 and by extension with inlet 120a and outlet 120b. The apertures 125 allow a flow of air or other fluid through the chamber to create suction between the breast tissue and the plate 104b. Stabilization of breast tissue via suction is described in detail in U.S. Pat. Nos. 6,304,770 and 7,828,744, both of which are incorporated by reference.

Figure 13:
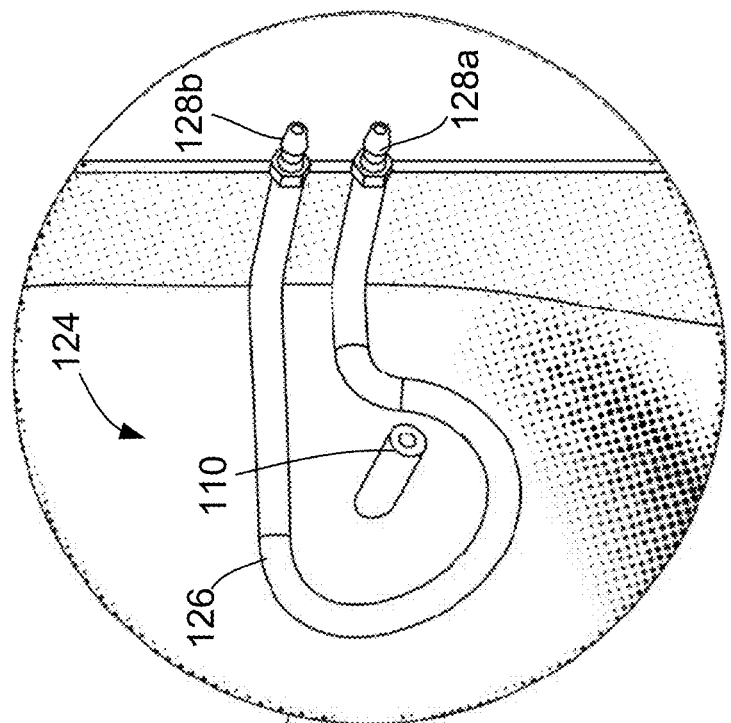
FIG. 13 is an enlarged cross-sectional view of the guidance template of FIG. 12 illustrating a tube of the temperature management assembly and associated inlet and outlet ports allowing for a recirculating coolant fluid to flow through the tube.
Figure 12:
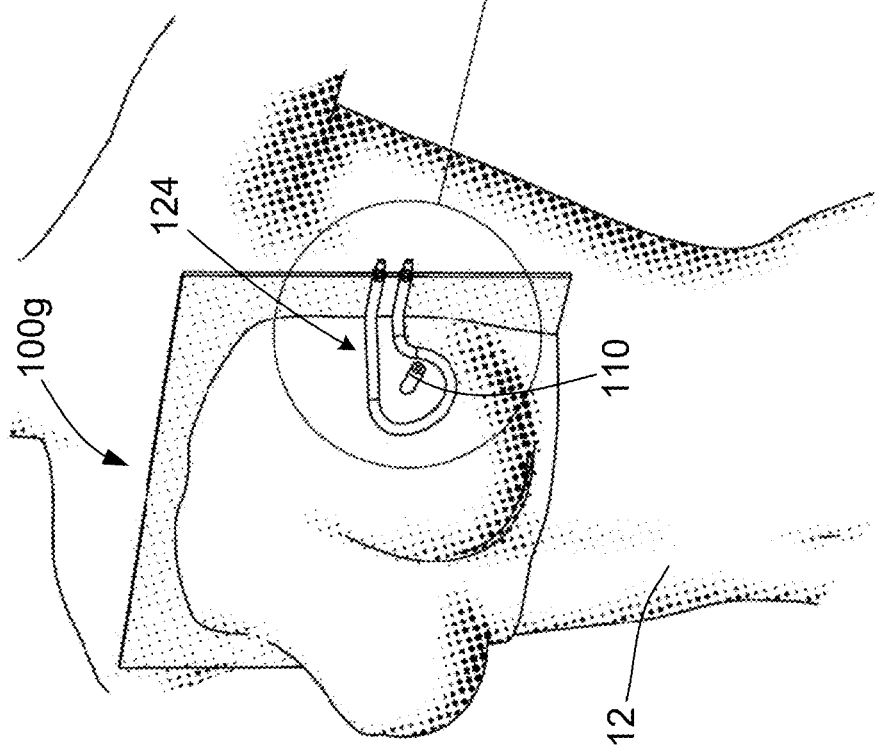
FIG. 12 is a front perspective view of another embodiment of a guidance template consistent with the present disclosure, wherein the guidance template comprises a temperature management assembly.
Figure 14:
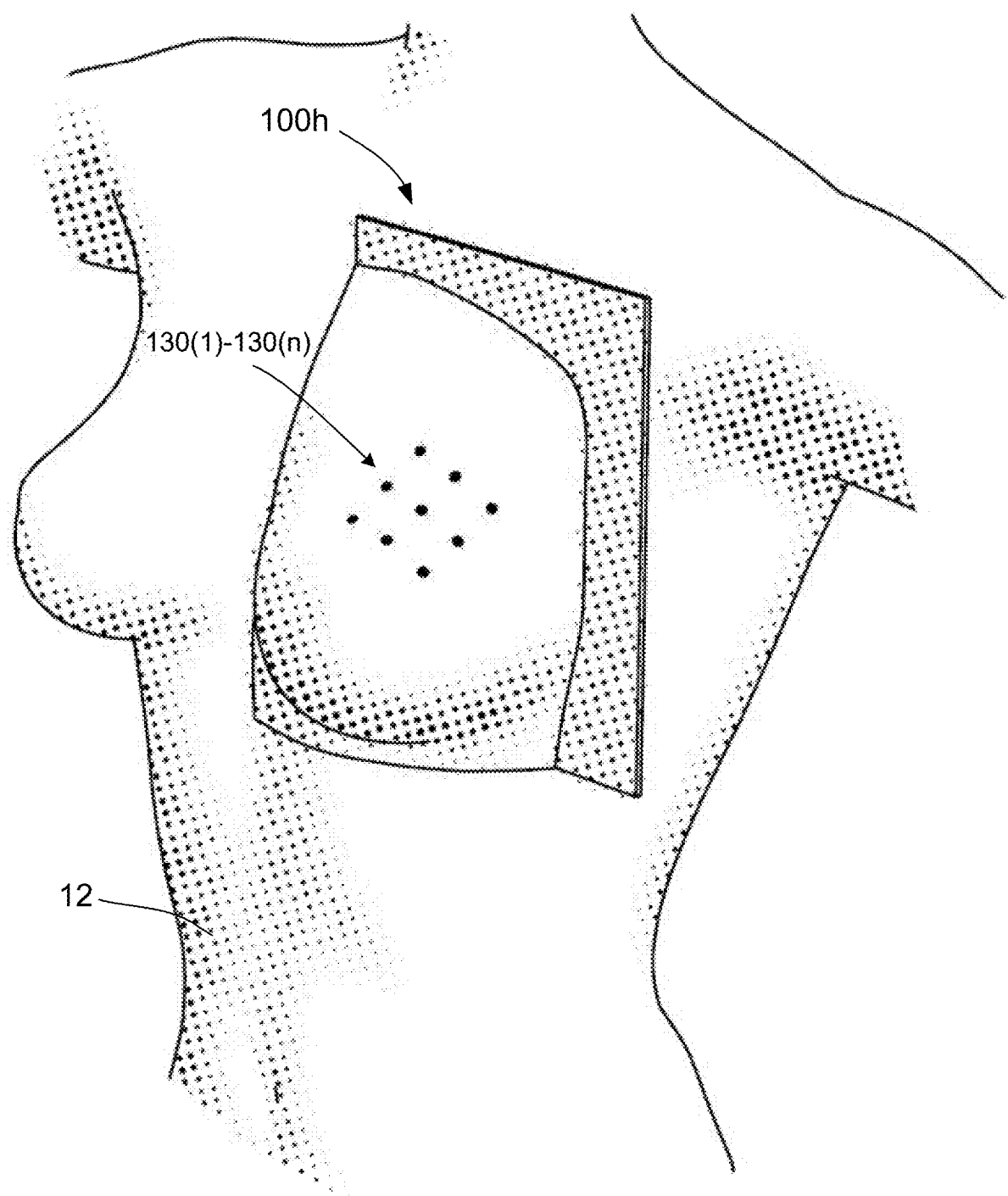
FIG. 14 is a side perspective view of another embodiment of a guidance template consistent with the present disclosure, wherein the guidance template comprises a plurality of access sites integrally formed on the cover and in a particular pattern related to injection sites relative to a portion of the breast to undergo a tissue treatment or removal procedure.

FIG. 12 is a front perspective view of another embodiment of a guidance template 100g consistent with the present disclosure and FIG. 13 is an enlarged cross-sectional view of the guidance template 100g. In the instance that the specific procedure involves application of thermal energy in a confined region of the breast, the guidance template 100g may include a temperature management assembly 124 that simply includes a length of tubing 126 integrally formed with the guidance template 100g and includes an inlet 128a and an outlet 128b at either end thereof. The single tube 126 may be arranged about the region in which the procedure is to be performed. For example, the tubing 126 may simply circumscribe an access site, such that, the temperature of any breast tissue or skin surface adjacent the access site will be maintained. FIG. 14 is a side perspective view of another embodiment of a guidance template 100h consistent with the present disclosure, wherein the guidance template 100h comprises a plurality of access sites 130(1)-130(n) integrally formed on the cover portion and in a particular pattern related to injection sites relative to a portion of the breast to undergo a tissue treatment or removal procedure. For example, the trend toward office-based procedures continues, and procedures that don't require general anesthesia will become office-based procedures.

Accordingly, percutaneous needle procedures, such as needle biopsies can be performed under regional-local anesthetics that are delivered directly into the target tissue. The plurality of access sites 130(1)-130(n) may provide for specific locations for needle injections for the delivery of anesthesia into the appropriate pattern.

Figure 16:
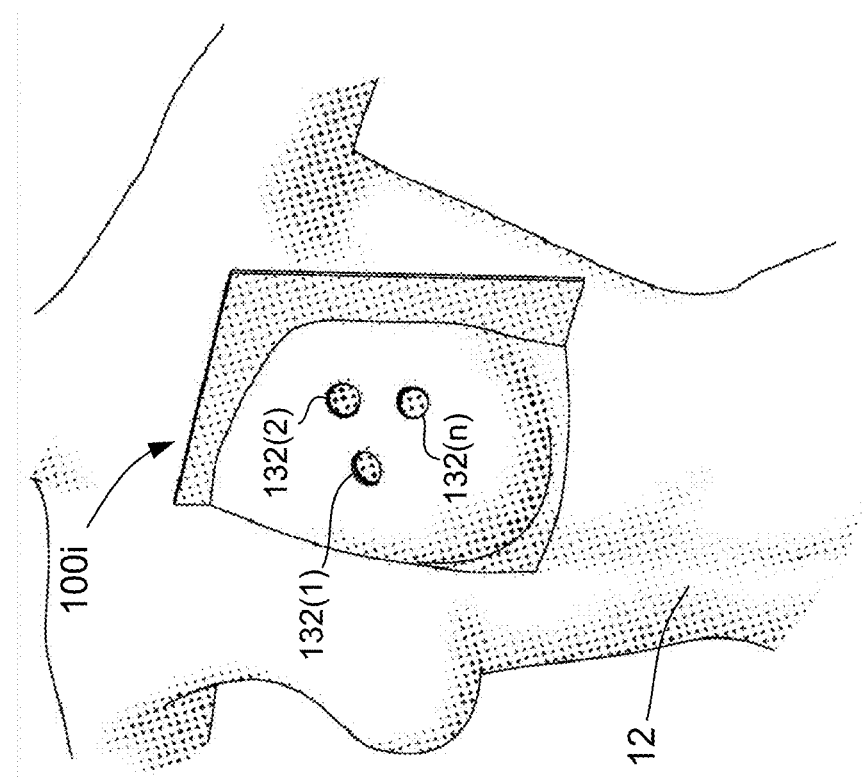
FIG. 16 is a perspective view on another embodiment of a guidance template consistent with the present disclosure, wherein the guidance template comprises base reference points corresponding to the markers on the patient's breast and acting as an alignment aid.
Figure 15:
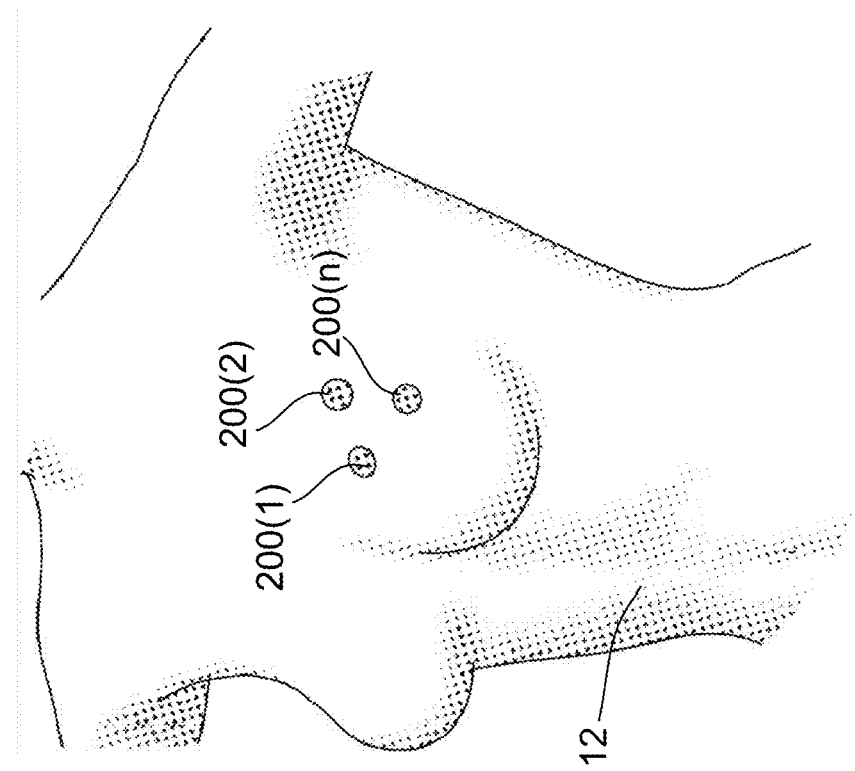
FIG. 15 is a perspective view of a patient's breasts, in which one breast includes markers, generally placed at the time of imaging to provide anatomical landmarks.

FIG. 15 is a perspective view of a patient's breasts, in which one breast includes markers 200(1), 200(2), and 200(3), generally placed at the time of imaging to provide anatomical landmarks to enhance placement and alignment of a guidance template upon the breast. FIG. 16 is a perspective view on another embodiment of a guidance template 100i consistent with the present disclosure, wherein the guidance template 100i comprises base reference points 132(1), 132(2), and 132(3) corresponding to the markers 200(1), 200(2), and 200(3) on the patient's breast and acting as an alignment aid. Markers 200 that can be used are ones that are MRI compatible, but visible under MR imaging. For example, one type of marker may include a dressing, such as TEGADERM Alginate Ag Silver Dressing, available from 3M (Maplewood, Minn.). The dressings 200 can be placed on the desired location on the patient's breast and, upon performing an imaging procedure, the dressings 200 will be captured in the imaging data. Accordingly, the guidance template constructed from the imaging data can include reference points 132, which may be in the form of voids or the like, that correspond to the pattern of the placement of the dressings 200 upon the breast. Accordingly, upon placement of the guidance template upon the breast, a surgeon need only align the reference points 132 with the corresponding dressings 200 (which remain on the breast), thereby ensuring that the template is in the correct and intended position.

Figure 17:
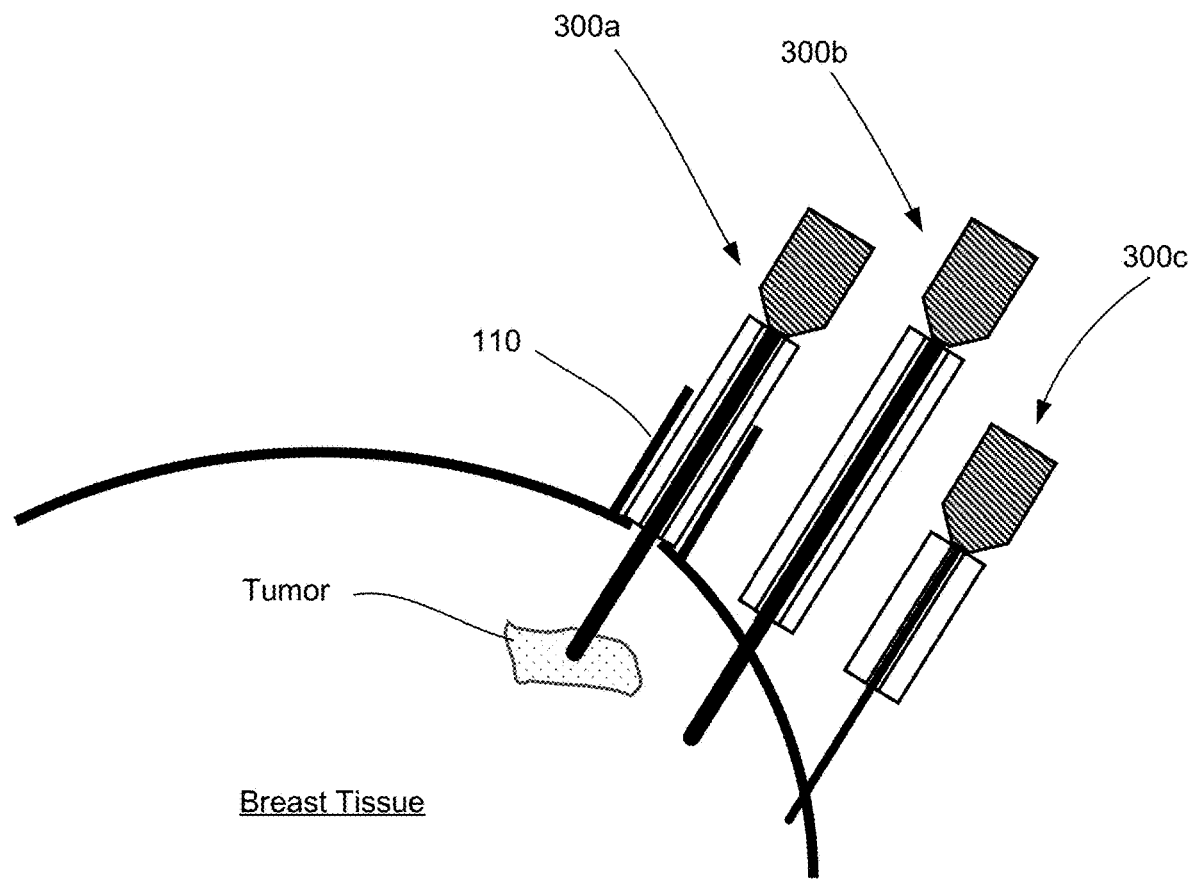
FIG. 17 is a side view, partly in section, of adapters for coupling biopsy, injection, or surgical devices to standardized access sites or ports defined on the guidance template.

FIG. 17 is a side view, partly in section, of adapters 300a, 300b, 300c for coupling different biopsy, injection, or surgical devices to a standardized access site 110 or port defined on the guidance template 100. In some embodiments, the access site or port 110 may be a standard size. In other words, while each cover portion 104 may have a patient-specific shape and one or more access sites 110 may be placed in specific locations on the cover portion 104, each access site 110 may have a standard length and diameter. The coupling adapters 300 may be shaped and/or sized to be cooperatively coupled to a standardized access site 110, while allowing for different-sized devices to access the tissue abnormality using the same access site 110. The use of standardized access sites allows for flexibility in manufacturing, as there is one less customized aspect of the guidance template required. Furthermore, by provided a standardized access site, through which multiple devices can access the target tissue, allows for a variety of different procedures to be performed, including, but not limited to, combination therapies, imaging/sensing effectiveness post procedure, as well as surveying/sensing pre therapy. For example, in the illustrated embodiment, precise coupling adapters 300a, 300b, and 300c, allow sequential targeting of a specific location in tissue with multiple devices of different diameters and lengths (e.g. allow treating with devices (a and b) and in situ assessment with device (c) through same port).

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed is:

1. A guidance template device for providing guidance for a targeted tissue treatment or tissue removal procedure, the guidance template device comprising:
a cover portion shaped and sized to fit over a surface of a patient near a target tissue to undergo a treatment or removal procedure, the cover portion including at least one form including a patient-specific interior surface customized based on images obtained during pre-procedure imaging to match the surface of the patient such that the cover portion correspondingly fits over the surface of the patient and maintains the surface of the patient in a desired position;
at least one access site integrally formed with the cover portion, the at least one access site positioned so as to direct a working end of a first medical device to a location associated with the target tissue when the cover portion is placed on the surface of the patient, the position of the at least one access site with respect to the target tissue having been determined based on the pre-procedure images; and
at least one imaging jig integrally formed with the cover portion and configured to retain an in-procedure imaging device therein and further configured to control positioning and/or movement of the in-procedure imaging device relative to the location associated with the target tissue when the cover portion is placed on the surface of the patient.

2. The guidance template device of claim 1, wherein the first medical device is selected from the group consisting of a biopsy device, an injection device, and a surgical device.

3. The guidance template device of claim 2, wherein the surgical device comprises a working end configured to ablate or resect the target tissue.

4. The guidance template device of claim 2, wherein the imaging jig is configured to guide positioning and/or movement of the first medical device relative to the access site by registering the in-procedure images with the images obtained during pre-procedure imaging.

5. The guidance template device of claim 1, wherein the in-procedure imaging device comprises an ultrasound transducer wand.

6. The guidance template device of claim 5, wherein the imaging jig comprises a socket portion configured to provide a friction fit with a working end of the ultrasound transducer wand and further provide controlled movement thereof relative to the location associated with the target tissue.

7. The guidance template device of claim 1, wherein the target tissue comprises a tissue abnormality in a breast of the patient, and wherein the interior surface of the form of the cover portion is configured to match a surface of the breast.

8. The guidance template device of claim 1, wherein the cover portion is constructed via an additive manufacturing process based on a fabrication instruction file including imaging data of the surface of the patient and the target tissue to undergo a treatment or removal procedure.

9. The guidance template device of claim 8, wherein the imaging data is obtained via pre-procedure imaging while the patient is in a supine position.

10. The guidance template device of claim 9, wherein the pre-procedure imaging comprises magnetic resonance imaging (MRI).

11. The guidance template device of claim 9, wherein the imaging data comprises at least one of surface data related to a surface contour of at least one of the patient's breasts, volumetric data related to a volume of the breast, spatial properties of the tissue abnormality (i.e., tumor) within the breast, as well as the position of the tissue abnormality within the breast.

12. The guidance template device of claim 8, wherein the access site and imaging jig are constructed via the additive manufacturing process based on a fabrication instruction file including procedural data related to the specific tissue treatment or tissue removal procedure to be performed on the target tissue.

13. The guidance template device of claim 1, wherein the cover portion comprises at least one reference point defined thereon, wherein a shape and/or size of the reference point and a positioning of the reference point on the cover portion is configured to correspond to a shape and/or size of an associated marker and a positioning of the associated marker on the surface of the patient.

14. The guidance template device of claim 1, wherein the cover portion comprises a plurality of apertures configured to create suction between the surface of the patient and the interior surface.

15. The guidance template device of claim 1, wherein the imaging jig is configured to orient the in-procedure imaging device to align with an imaging plane of the images obtained during the pre-procedure imaging.

16. The guidance template device of claim 1, wherein the in-procedure imaging device obtains images in a different modality than the pre-procedure images.

17. A guidance template device for providing guidance for a targeted tissue treatment or tissue removal procedure, the guidance template device comprising:
   a cover portion shaped and sized to fit over a surface of a patient near a target tissue to undergo a treatment or removal procedure, the cover portion including at least one form including a patient-specific interior surface customized based on images obtained during pre-procedure imaging to match the surface of the patient such that the cover portion correspondingly fits over the surface of the patient and maintains the surface of the patient in a desired position;
   at least one access site integrally formed with the cover portion, the at least one access site positioned so as to direct a working end of an electrosurgical device to a location associated with the target tissue when the cover portion is placed on the surface of the patient, the position of the at least one access site with respect to the target tissue having been determined based on the pre-procedure images, wherein the working end of the electrosurgical device is configured to apply energy to the target tissue;
   at least one imaging jig integrally formed with the cover portion and configured to retain an in-procedure imaging device therein and further configured to control positioning and/or movement of the in-procedure imaging device relative to the location associated with the target tissue when the cover portion is placed on the surface of the patient; and
   a temperature management assembly integrally formed with the cover portion and positioned so as to maintain a temperature of surrounding or adjacent tissue relative to the target tissue upon application of energy to the target tissue from the working end of the electrosurgical device to thereby prevent damage to the surrounding or adjacent tissue when the cover portion is placed on the surface of the patient.

18. The guidance template device of claim 17, wherein the temperature management assembly comprises at least one chamber positioned between the interior surface and an exterior of the at least one form, the at least one chamber in fluid communication with at least one inlet port and at least one outlet port and configured to receive a recirculating coolant fluid therefrom.

19. The guidance template device of claim 18, wherein the cover portion comprises a first plate serving as an interior surface and a second plate serving as an exterior surface, wherein the chamber is defined therebetween.

20. The guidance template device of claim 18, wherein the coolant fluid comprises a gas or a liquid.

21. The guidance template device of claim 18, wherein the interior surface comprises a plurality of apertures in fluid communication with the at least one chamber, the plurality of apertures configured to create suction between the surface of the patient and the cover portion when the fluid flows through the chamber.

22. The guidance template device of claim 17, wherein the temperature management assembly comprises a length of tubing comprising an inlet port and an outlet port at either end thereof and configured to receive a recirculating coolant fluid therefrom.

23. The guidance template device of claim 22, wherein the length of tubing circumscribes a defined area of the form of the cover portion so as to provide a confined area of temperature management relative to the location associated with the target tissue when the cover portion is placed on the surface of the patient.

* * * * *

UNITED STATES PATENT AND TRADEMARK OFFICE
CERTIFICATE OF CORRECTION

PATENT NO. : 10,555,791 B2
APPLICATION NO. : 16/437915
DATED : February 11, 2020
INVENTOR(S) : Venkataramanan Krishnaswamy et al.

It is certified that error appears in the above-identified patent and that said Letters Patent is hereby corrected as shown below:

On the Title Page

Item (63), application No. PCT/US2016/029708 should be changed to application No. PCT/US2019/029708

Signed and Sealed this
Twelfth Day of January, 2021

Andrei Iancu
*Director of the United States Patent and Trademark Office*